US012648701B2

(12) United States Patent
Kawabe

(10) Patent No.: US 12,648,701 B2
(45) Date of Patent: Jun. 9, 2026

(54) INFORMATION PROCESSING APPARATUS, LIVING BODY DETECTION SYSTEM, LIVING BODY DETECTION METHOD, AND RECORDING MEDIA

(71) Applicant: NEC Corporation, Tokyo (JP)

(72) Inventor: Tomoyuki Kawabe, Tokyo (JP)

(73) Assignee: NEC CORPORATION, Tokyo (JP)

( * ) Notice: Subject to any disclaimer, the term of this patent is extended or adjusted under 35 U.S.C. 154(b) by 540 days.

(21) Appl. No.: 18/022,859

(22) PCT Filed: Sep. 30, 2020

(86) PCT No.: PCT/JP2020/037221
§ 371 (c)(1),
(2) Date: Feb. 23, 2023

(87) PCT Pub. No.: WO2022/070331
PCT Pub. Date: Apr. 7, 2022

(65) Prior Publication Data
US 2023/0320593 A1     Oct. 12, 2023

(51) Int. Cl.
| | |
|---|---|
| *A61B 5/01* | (2006.01) |
| *A61B 5/00* | (2006.01) |
| *A61B 5/1171* | (2016.01) |
| *F24F 11/56* | (2018.01) |
| *G06N 20/00* | (2019.01) |
| *G06T 7/00* | (2017.01) |

(52) U.S. Cl.
CPC .............. *A61B 5/01* (2013.01); *A61B 5/0077* (2013.01); *A61B 5/1176* (2013.01); *G06T 7/0016* (2013.01)

(58) Field of Classification Search
CPC ....... A61B 5/01; A61B 5/0077; A61B 5/1176; G06T 7/0016; F24F 11/56; G06N 20/00
See application file for complete search history.

(56) References Cited

U.S. PATENT DOCUMENTS

| | | | | |
|---|---|---|---|---|
| 2010/0046505 A1* | 2/2010 | Saw | .................... | H04M 1/2535 |
| | | | | 370/352 |
| 2014/0153777 A1* | 6/2014 | Nagaoka | ................ | G08G 1/166 |
| | | | | 382/103 |
| 2014/0330560 A1* | 11/2014 | Venkatesha | ............. | G06F 21/32 |
| | | | | 704/235 |
| 2019/0309978 A1* | 10/2019 | Song | ........................ | F24F 11/56 |

(Continued)

FOREIGN PATENT DOCUMENTS

| | | |
|---|---|---|
| JP | 2003-534864 A | 11/2003 |
| JP | 2007-037652 A | 2/2007 |

(Continued)

OTHER PUBLICATIONS

Computer translation of JP 6742554 downloaded from the JPO website on Jun. 26, 2025.*

(Continued)

*Primary Examiner* — Randy W Gibson
(74) *Attorney, Agent, or Firm* — Sughrue Mion, PLLC

(57) ABSTRACT

The apparatus according to this disclosure includes object temperature change measuring means for measuring a temperature change of a surface temperature of an object, and living body determination means for determining whether or not the object is a living body based on the temperature change.

15 Claims, 28 Drawing Sheets

(56)     References Cited

U.S. PATENT DOCUMENTS

| | | | |
|---|---|---|---|
| 2020/0175291 A1 | 6/2020 | Kitchens et al. | |
| 2020/0394387 A1* | 12/2020 | Chen ................... | G06V 10/143 |

FOREIGN PATENT DOCUMENTS

| | | |
|---|---|---|
| JP | 2014-093693 A | 5/2014 |
| JP | 2017-015288 A | 1/2017 |
| JP | 2017-191374 A | 10/2017 |
| JP | 2020-062198 A | 4/2020 |
| JP | 6742554 B1 | 8/2020 |
| WO | 2012/114474 A1 | 8/2012 |
| WO | 2019/238251 A1 | 12/2019 |

OTHER PUBLICATIONS

Japanese Office Action for JP Application No. 2022-553325 mailed on Jan. 23, 2024 with English Translation.
International Search Report for PCT Application No. PCT/JP2020/037221, mailed on Nov. 24, 2020.
Extended European Search Report for EP Application No. 20956259.4, dated on Oct. 30, 2023.

\* cited by examiner

TEMPERATURE

TIME

INFORMATION PROCESSING APPARATUS, LIVING BODY DETECTION SYSTEM, LIVING BODY DETECTION METHOD, AND RECORDING MEDIA

This application is a National Stage Entry of PCT/JP2020/037221 filed on Sep. 30, 2020, the contents of all of which are incorporated herein by reference, in their entirety.

TECHNICAL FIELD

The present disclosure relates to an information processing apparatus, a living body detection system, a living body detection method, and a recording media.

BACKGROUND ART

For example, Patent Literature 1 discloses a living body determination apparatus configured to determine whether an object is a living body, based on the feature values obtained from a first image taken by irradiating the object with light in a first wavelength range and the feature values obtained from a second image taken by irradiating the object with light in a second wavelength range.

CITATION LIST

Patent Literature

Patent Literature 1: Japanese Unexamined Patent Application Publication No. 2017-191374

SUMMARY OF INVENTION

Technical Problem

This disclosure is intended to improve upon the techniques disclosed in the prior art documents described above.

Solution to Problem

An information processing apparatus according to a first aspect of this disclosure includes: object temperature change measuring means for measuring a temperature change of a surface temperature of an object, and
living body determination means for determining whether or not the object is a living body based on the temperature change.

A living body detection system according to a second aspect of this disclosure includes: object temperature change measuring means for measuring a temperature change of a surface temperature of an object, and
living body determination means for determining whether or not the object is a living body based on the temperature change.

A living body detection method according to a third aspect of this disclosure includes: object temperature change measuring step measuring a temperature change of a surface temperature of an object, and
living body determination step determining whether or not the object is a living body based on the temperature change.

A recording media according to a fourth aspect of this disclosure is a non-transitory computer readable medium storing a program for causing an electronic device to execute the following steps of: object temperature change measuring step measuring a temperature change of a surface temperature of an object, and living body determination step determining whether or not the object is a living body based on the temperature change.

EXAMPLE EMBODIMENT

First Embodiment

First, a configuration example of a living body detection apparatus 10 according to a first embodiment will be described with reference to FIG. 1. The living body detection apparatus 10 is an example of an information processing apparatus of the present invention.

Figure 1:
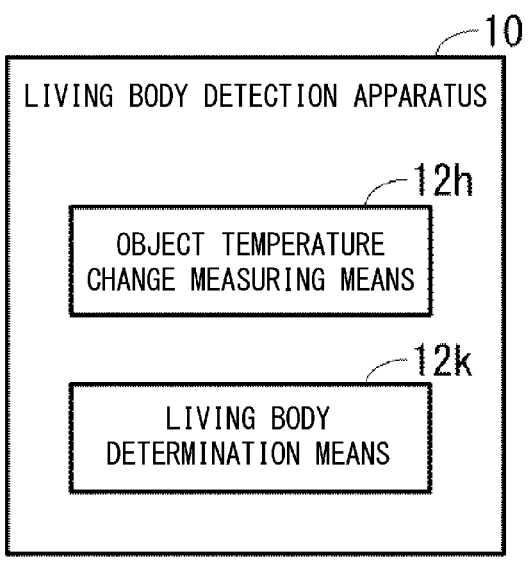
FIG. 1 is a schematic diagram of the living body detection apparatus 10.

FIG. 1 is a schematic diagram of the living body detection apparatus 10.

As shown in FIG. 1, the living body detection apparatus 10 comprises object temperature change measuring means 12h for measuring a temperature change of a surface temperature of an object, and living body determination means 12k for determining whether or not the object is a living body, based on the temperature change measured by the object temperature change measuring means 12h.

Next, an example of an operation of the living body detection apparatus 10 with the above configuration will be described.

Figure 2:
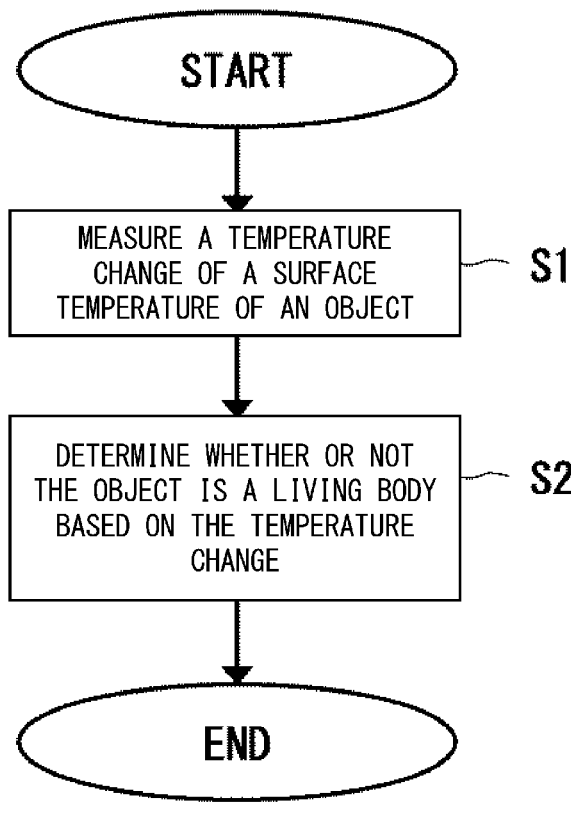
FIG. 2 is a flowchart of one example of an operation of the living body detection apparatus 10.

FIG. 2 is a flowchart of one example of an operation of the living body detection apparatus 10.

First, the object temperature change measuring means 12h measures a temperature change of a surface temperature of an object (step S1). Next, the living body determination means 12k determines whether or not the object is a living body based on the temperature change measured by the object temperature change measuring means 12h (step S2).

As described above, according to the first embodiment, a disguisement using an elaborate 3D mask or a disguisement (for example, impersonation during face authentication) using a life-size mask using a photograph with the eyes and mouth cut out can be detected.

This is because whether or not an object is a living body is determined based on the temperature change of the surface (for example, the face) temperature of the object, not the surface (for example, the face) temperature of the object.

Second Embodiment

Hereafter, a living body detection system 1 and the living body detection apparatus 10 are described in detail as a second embodiment of this disclosure.

Figure 3:
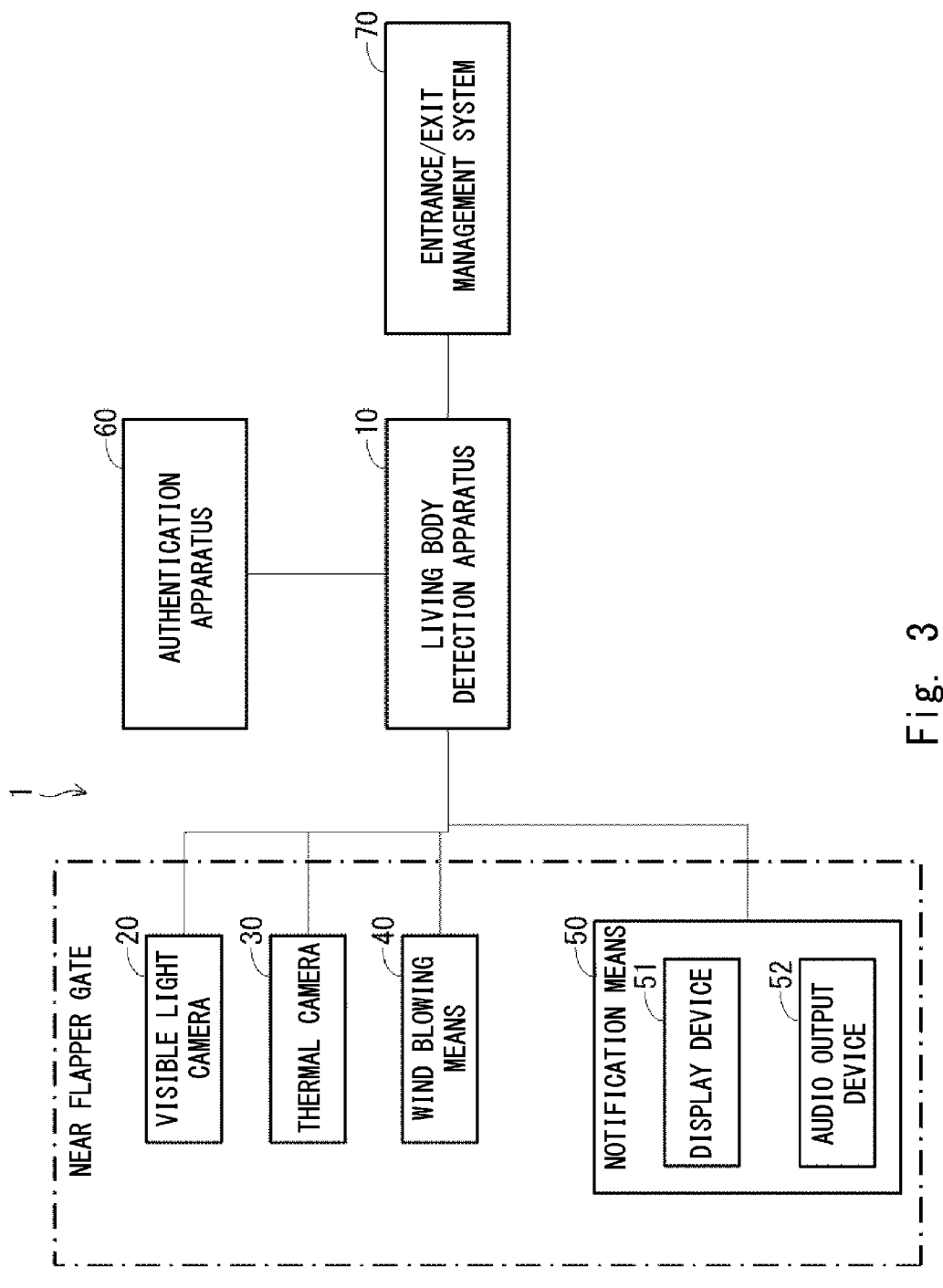
FIG. 3 is a block diagram showing the configuration of the living body detection system 1 according to the second embodiment.

FIG. 3 is a block diagram showing the configuration of the living body detection system 1 according to the second embodiment.

The living body detection system 1 is a system configured to determine (detect) whether or not an object is a living body.

The living body detection system 1 comprises a living body detection apparatus 10, a visible light camera 20, a thermal camera 30, wind blowing means 40, notification means 50, an authentication apparatus 60, and an entrance/exit management system 70. They can communicate with each other via communication lines (for example, the Internet). Note that the authentication apparatus 60 may be provided in the living body detection apparatus 10.

First, a configuration example of the living body detection apparatus 10 will be described.

Figure 4:
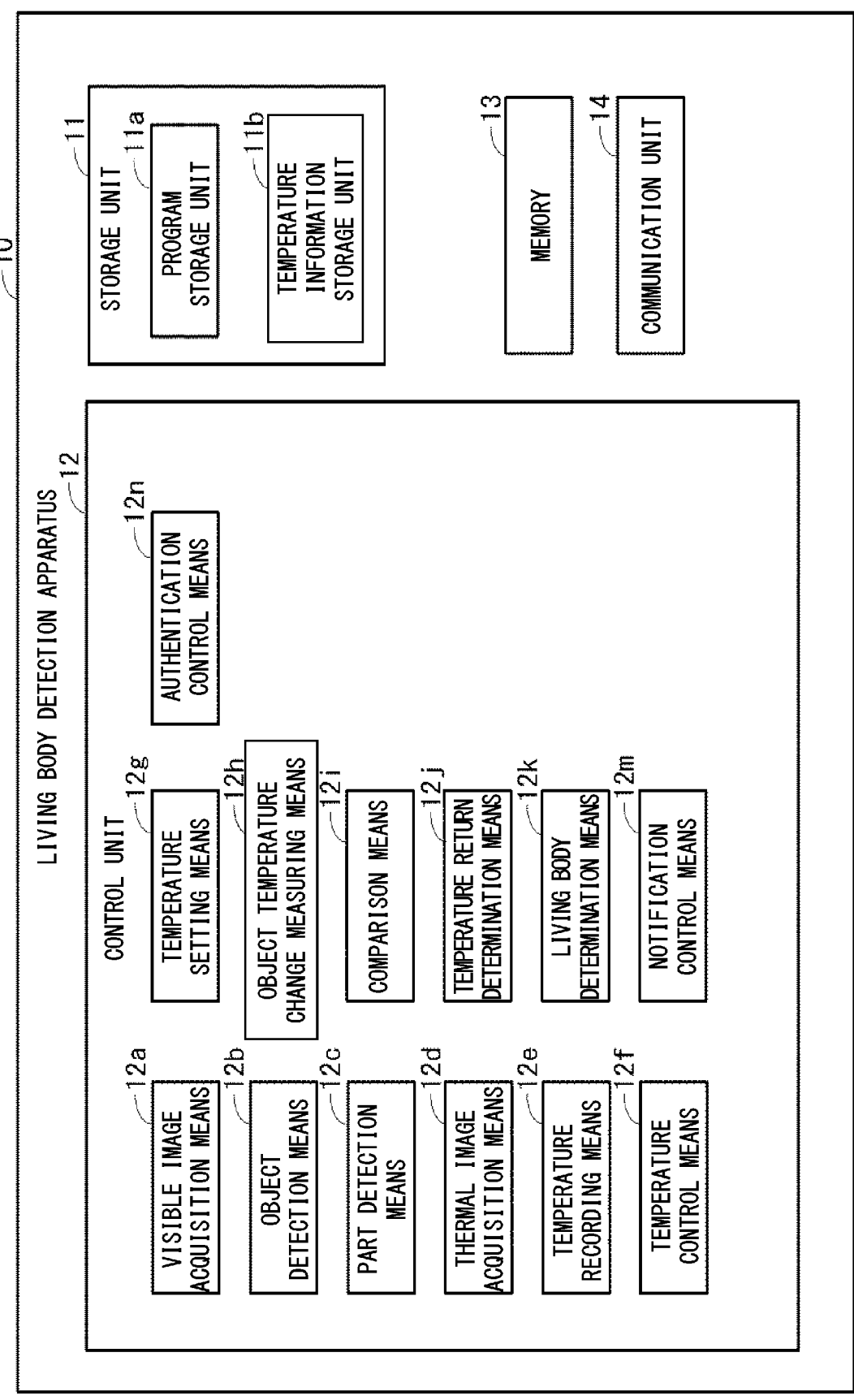
FIG. 4 is a schematic diagram of the living body detection apparatus 10.

FIG. 4 is a schematic diagram of the living body detection apparatus 10. The living body detection apparatus 10 can be realized by an information processing apparatus such as a personal computer, for example.

As shown in FIG. 4, the living body detection apparatus 10 includes a storage unit 11, a control unit 12, a memory 13, and a communication unit 14.

The storage unit 11 is, for example, a non-volatile storage unit such as a hard disk drive or a ROM. The storage unit 11 includes a program storage unit 11a and a temperature information storage unit 11b.

A program to be executed by the control unit 12 (a processor) is stored in the program storage unit 11a. In the temperature information storage unit 11b, temperature information for each object part is stored by temperature recording means 12e.

The control unit 12 has a processor (not shown). The processor is, for example, a CPU (Central Processing Unit), but is not limited to this and may be a GPU (Graphics Processing Unit), FPGA (Field-Programmable Gate Array), DSP (Digital Signal Processor), or ASIC (Application Specific Integrated Circuit). The processor can be a single processor or multiple processors. The program storage unit 11a stores software modules that define processes for functioning as visible image acquisition means 12a, object detection means 12b, part detection means 12c, thermal image acquisition means 12d, temperature recording means 12e, temperature control means 12f, temperature setting means 12g, object temperature change measuring means 12h, comparison means 12i, temperature return determination means 12j, living body determination means 12k, notification control means 12m, and authentication control means 12n. By executing the program read from the program storage unit 11a into the memory 13 (for example, RAM), the processor functions as the visible image acquisition means 12a, the object detection means 12b, the part detection means 12c, the thermal image acquisition means 12d, the temperature recording means 12e, the temperature control means 12f, the temperature setting means 12g, the object temperature change measuring means 12h, the comparison means 12i, the temperature return determination means 12j, the living body determination means 12k, the notification control means 12m, and the authentication control means 12n. A part or all of these may be realized by hardware.

The visible image acquisition means 12a acquires from the visible light camera 20 a visible image including an object taken by the visible light camera 20. The object is, for example, a person (a living body) attempting to perform face authentication, a person (non-living body) in a photograph (or video) displayed on a display such as a tablet, a person (non-living body) in a paper photograph, or a person (non-living body) wearing a 3D mask.

The object detection means 12b detects the object (a face area) in the visible image acquired by the visible image acquisition means 12a.

The part detection means 12c detects at least one part (ears, nose, forehead, cheeks, for example) in the object (in the face area) detected by the object detection means 12b. For example, the part detection means 12c detects a first part that is relatively likely to change temperature (ears, nose, for example) and a second part that is relatively unlikely to change temperature (for example, forehead, cheeks). The first part that is relatively likely to change temperature is the part of the body that is more temperature-changeable than the second part, e.g., ears, nose. The second part that is relatively unlikely to change temperature is the part of the body that is more temperature-non-changeable than the first part, e.g., forehead and cheeks. Note that the number of the first part and the second part detected by the part detection means 12c may be one, or may be plural respectively.

The thermal image acquisition means 12d acquires from the thermal camera 30 a thermal image (for example, see signs 11-13 in FIG. 5) including the object taken by the thermal camera 30.

The temperature recording means 12e stores temperature information of a surface temperature of each part (in the thermal image acquired by the thermal image acquisition means 12d) detected by the part detection means 12c in the temperature information storage unit 11b.

Figure 5:
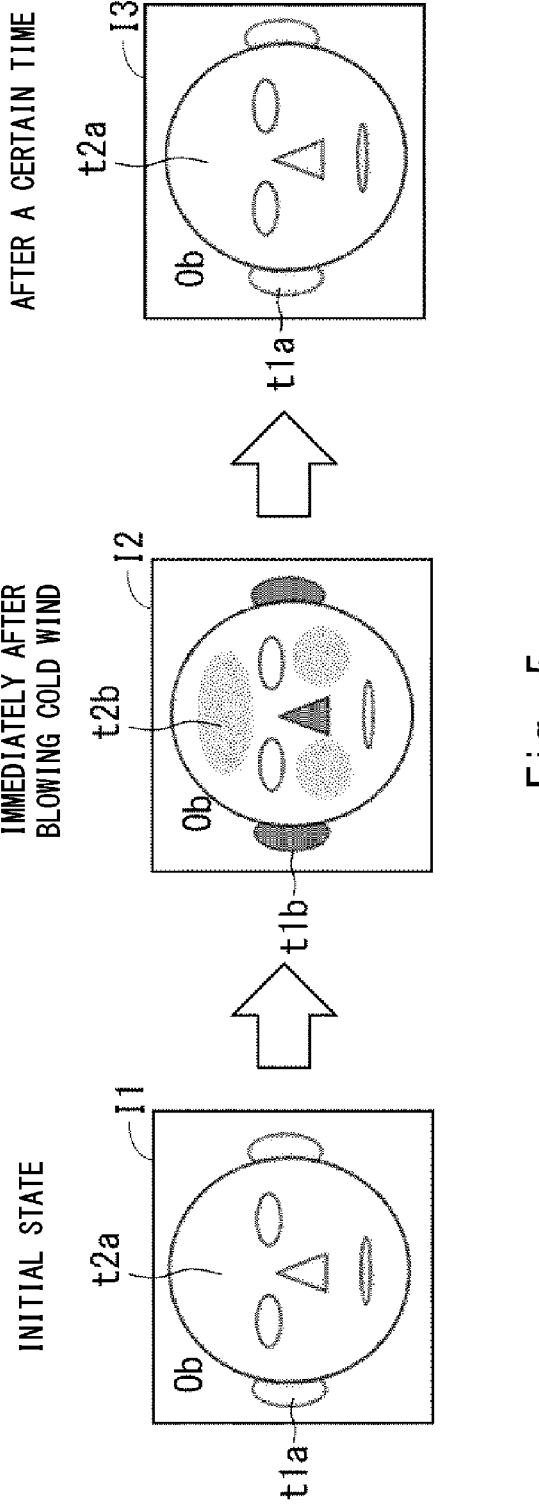
FIG. 5 shows an example of thermal images 11-13.

For example, it is assumed that the object detection means 12b detects the ears as the first part that is relatively likely to change temperature and forehead as the second part that is relatively unlikely to change temperature. Then, as shown in FIG. 5, it is assumed that the surface temperature of the ears changes in the order of t1a, t1b, and t1a, and the surface temperature of the forehead changes in the order of t2a, t2b, and t2a. In this case, the temperature recording means 12e stores the surface temperatures t1a, t1b and t1a of the ears and the surface temperatures t2a, t2b and t2a of the forehead in the temperature information storage unit 11b as temperature information of the surface temperature of each part. FIG. 5 shows an example of thermal images 11-13. Note that in FIG. 5, the temperature is lower in the darker areas (the ears, for example) than in the lighter areas (for example, the forehead).

The temperature control means 12f controls the wind blowing means 40. For example, the temperature control means 12f controls the wind blowing means 40 so as to blow a wind (for example, a cool wind) of a predetermined temperature (the temperature set by the temperature setting means 12g) to the object's face at a predetermined timing for a predetermined time.

The temperature setting means 12g sets a temperature (a predetermined temperature) of a wind blown by the wind blowing means 40. For example, the temperature setting means 12g sets the temperature inputted by an operator as the predetermined temperature. In addition, the temperature setting means 12g may calculate a predetermined temperature at which a temperature change of a surface temperature of the object occurs based on the ambient temperature of a space in which the object exists or the surface temperature of the object, etc., and set the calculated temperature as the predetermined temperature. The ambient temperature of the space in which the object exists is, for example, the ambient temperature of the space near the object to be taken by the thermal camera 30. The ambient temperature of the space in which the object exists can be detected, for example, by a temperature sensor (not shown) provided near a flapper gate (for example, near the thermal camera 30).

The object temperature change measuring means 12h measures a temperature change of a surface temperature of the object. For example, the object temperature change measuring means 12h measures the temperature change of the object detected by the object detection means 12b based on a thermal image.

Specifically, the object temperature change measuring means 12h measures a temperature change of an object (for example, the first part and the second part detected by the part detection means 12c) detected by the object detection means 12b, based on the temperature information of the surface temperature for each part stored in the temperature information storage unit 11b.

For example, it is assumed that the surface temperatures t1a and t1b of the ears and the surface temperatures t2a and t2b of the forehead are stored in the temperature information storage unit 11b as temperature information of the surface temperature of each part. In this case, the object temperature change measuring means 12h measures (calculates) the temperature change t1a-t1b of the surface temperature of the ears (the first part) and the temperature change t2a-t2b of the surface temperature of the forehead (the second part) as a temperature change of the surface temperature of the object.

The comparison means 12i compares the temperature change of the first part measured by the object temperature change measuring means 12h with the temperature change of the second part measured by the object temperature change measuring means 12h.

For example, when the object temperature change measuring means 12h measures (calculates) the temperature change t1a-t1b of the surface temperature of the ears (the first part) and the temperature change t2a-t2b of the surface temperature of the forehead (the second part) as the temperature change of the surface temperature of the object, the comparison means 12i compares the temperature change t1a-t1b of the surface temperature of the ears (the first part) with the temperature change t2a-t2b of the surface temperature of the forehead (the second part).

The temperature return determination means 12j determines whether or not the object surface temperature has returned to an original surface temperature before the change. Note that the temperature return determination means 12j may determine whether or not the object surface temperature has returned to a temperature close to the original surface temperature before the change.

The living body determination means 12k determines whether or not the object is a living body based on the temperature change of the surface temperature of the object (for example, the first part and the second part detected by the part detection means 12c) measured by the object temperature change measuring means 12h.

Specifically, the living body determination means 12k determines whether or not the object is a living body based on the comparison result of the comparison means 12i.

For example, when the comparison result of the comparison means 12i shows the temperature change (for example, t1a-t1b) of the surface temperature of the first part (ears, for example)>the temperature change (t2a-t2b) of the surface temperature of the second part (for example, forehead), the living body determination means 12k determines that the object is a living body. The reasons for this are as follows.

In other words, living bodies have peculiar temperature-changing characteristics. For example, specific parts (for example, ears and nose) of a face of a person (a living body) have narrow blood vessels and are easily affected by changes in an outside temperature. Conversely, parts other (for example, forehead, cheeks) than specific parts of the face of the person (a living body) are less affected by changes in an outside temperature.

Therefore, for example, when a wind (for example, a cold wind) of a predetermined temperature is blown on a person's face for a certain period of time, or when a person moves to a space with a different ambient temperature (for example, when a person moves from outside a building into the building cooled by an air conditioner), the specific part (e.g., ears and nose) has a relatively large change in temperature, and parts other (for example, forehead, cheeks) than the specific part has a relatively small change in temperature.

Therefore, when the object is a living body, the relationship is as follows: the temperature change (for example, t1a-t1b) of the surface temperature of the first part (ears, for example)>the temperature change (t2a-t2b) of the surface temperature of the second part (for example, forehead).

Therefore, when the comparison result of the comparison means 12$i$ shows the temperature change (for example, t1$a$-t1$b$) of the surface temperature of the first part (ears, for example)>the temperature change (t2$a$-t2$b$) of the surface temperature of the second part (for example, the forehead), the living body determination means 12$k$ determines that the object is a living body. Furthermore, when a difference between the two is larger than a threshold, the living body determination means 12$k$ may determine that the object is a living body.

In some cases, the living body determination means 12$k$ determines whether or not the object is a living body based on the determination result of the temperature return determination means 12$j$.

In other words, when the object is a living body, the object has a constant temperature, so it returns to an original temperature before the temperature change after a certain time, as shown in FIG. 5. Thus, for example, when a surface temperature of an object changed by blowing a predetermined temperature of a wind (for example, a cold wind) by the wind blowing means 40 returns to an original surface temperature before the change after a predetermined period, the living body determination means 12$k$ determines that the object is a living body.

In addition, when it can be predicted that a surface temperature of an object (a part) will return to an original surface temperature before the change before the surface temperature of the object (the part) returns to the original surface temperature before the change (for example, when this prediction can be made based on a differential value of the temperature change on the way that the surface temperature of the object returns to the original surface temperature before the change), the living body determination means 12$k$ determines that the object is a living body. In addition, the living body determination means 12$k$ may determine whether or not the object is a living body based on both a comparison result of the comparison means 12$i$ and a determination result of the temperature return determination means 12$j$.

The notification control means 12$m$ causes the notification means 50 to notify that a wind will blow from now on before the wind blowing means 40 blows the wind to the object.

The authentication control means 12$n$ causes the authentication apparatus 60 performing a face authentication to perform the face authentication of the object.

The visible light camera 20 is installed near a flapper gate (not shown), for example, and takes a visible image including an object that is about to pass through the flapper gate. The visible light camera 20 continuously takes images at regular intervals.

The thermal camera 30 is installed, for example, near the flapper gate (for example, adjacent to the visible light camera 20) and takes a thermal image including an object that is about to pass through the flapper gate. The thermal camera 30 continuously takes images at regular intervals in order to measure a temperature change of the object.

The wind blowing means 40 is installed, for example, near the flapper gate (for example, between the visible light camera 20 and the thermal camera 30). The wind blowing means 40 is an example of surface temperature change means in this disclosure. The wind blowing means 40 is, for example, a warm/cold air blower such as a blower. The wind blowing means 40 is installed so as to blow a wind from the front direction of an object, for example, in order to blow the wind uniformly. The wind blowing means 40 blows a wind of a predetermined temperature to an object (a face) at a predetermined timing for a predetermined time according to a control from the living body detection apparatus 10 (the temperature control means 12$f$). The wind blowing means 40 is not limited to one but may be plural. An example using multiple wind blowing means 40 will be described later as a variation. Note that the wind blowing means 40 may always continue blowing a wind.

Figure 6:
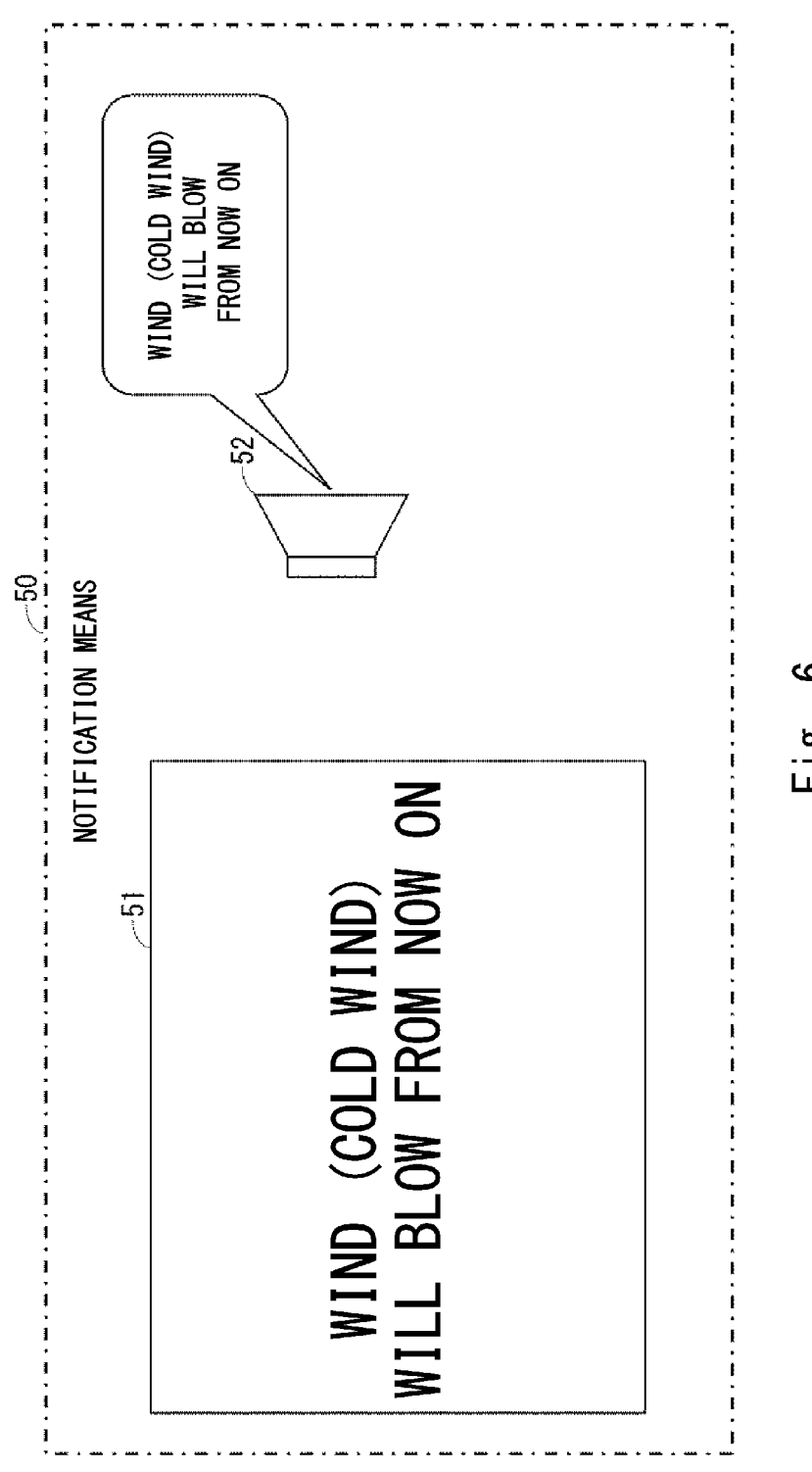
FIG. 6 shows an example of the contents notified by the notification means 50.

The notification means 50 is installed near the flapper gate, for example. The notification means 50 is, for example, a display device 51 such as a display or an audio output device 52 such as a speaker. The notification means 50 displays on the display device 51 that a wind will blow from now on, as shown in FIG. 6, before the wind blowing means 40 blows the wind to an object according to a control from the living body detection apparatus 10 (the notification control means 12$m$). At that time, it may display where the wind blows from and how long the wind blows. In addition, audio to that effect is output from the audio output device 52. FIG. 6 shows an example of the contents notified by the notification means 50.

In response to a face authentication request received from the living body detection apparatus 10, the authentication apparatus 60 collates with face feature information of a recognition object about a face image or face feature information included in the request, and returns the collation result to the living body detection apparatus 10 of the request source.

The entrance/exit management system 70 includes a flapper gate or the like. When the entrance/exit management system 70 receives the collation result from the living body detection apparatus 10, it controls the flapper gate according to the collation result.

The communication unit 14 is a communication apparatus that communicates with the visible light camera 20, the thermal camera 30, the wind blowing means 40, the notification means 50, the authentication apparatus 60 and the entrance/exit management system 70 via a communication line (for example, the Internet).

Next, an example of the operation of the living body detection apparatus 10 will be described.

Figure 7:
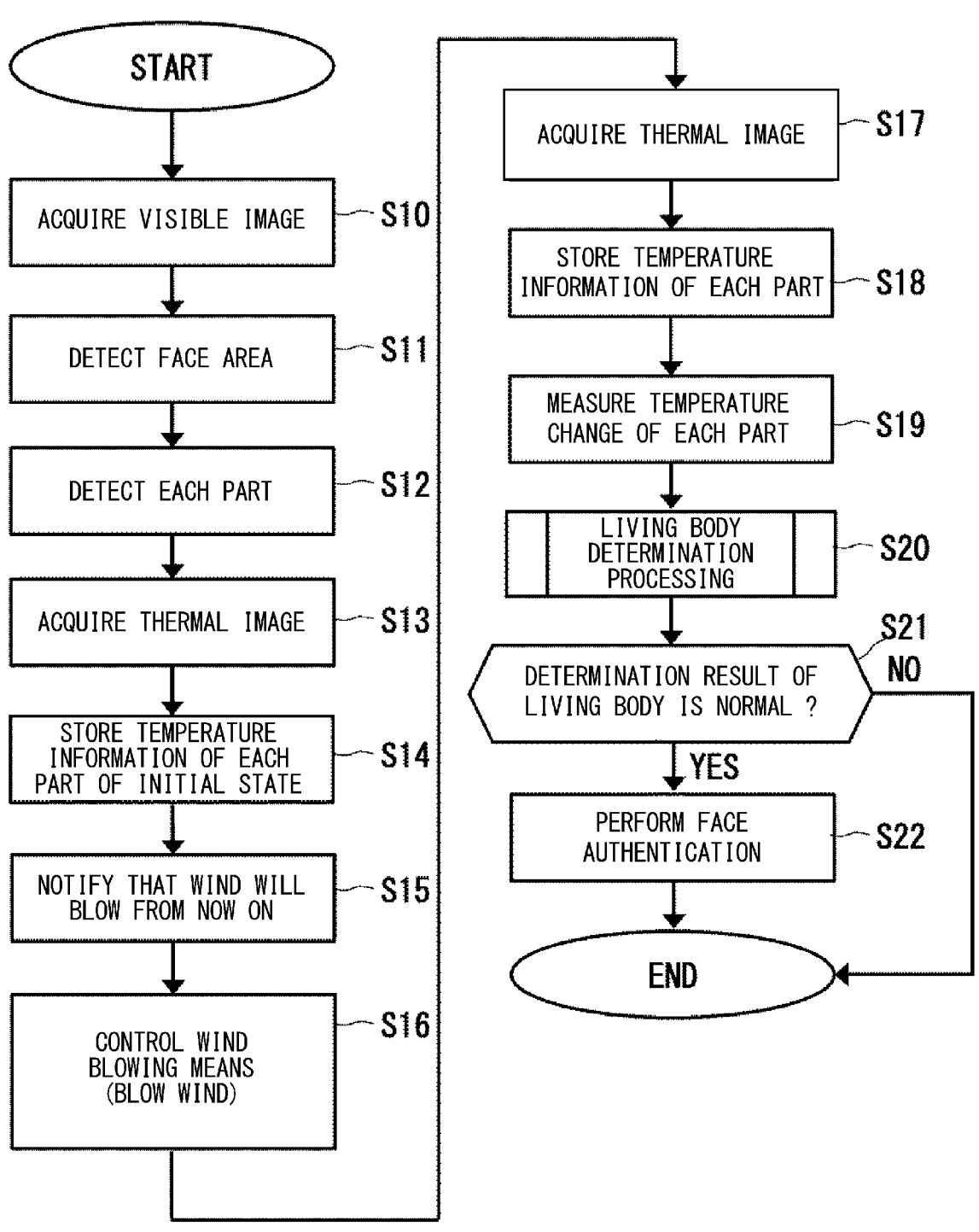
FIG. 7 is a flowchart of one example of the operation of the living body detection apparatus 10.

FIG. 7 is a flowchart of one example of the operation of the living body detection apparatus 10.

The following processing is realized by the control unit 12 (a processor) executing a program read from the program storage unit 11$a$ into a RAM (not shown).

Figure 8:
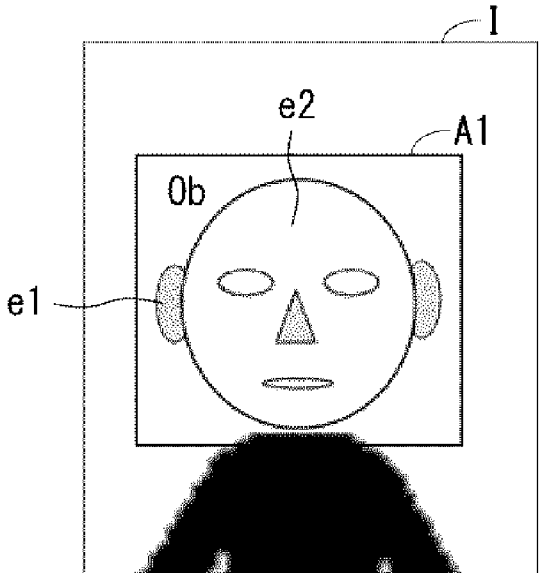
FIG. 8 is an example of a visible image I containing the face of the object Ob.

First, the visible image acquisition means 12$a$ acquires a visible image including an object taken by the visible light camera 20 from the visible light camera 20 (step S10). Here, it is assumed that a visible image I including the face of the object Ob shown in FIG. 8 is acquired. FIG. 8 is an example of a visible image I containing the face of the object Ob.

Next, the object detection means 12$b$ detects the face area A1 of the object Ob in the visible image I acquired by the visible image acquisition means 12$a$ (step S11).

Next, the part detection means 12$c$ detects each part (a first part that is relatively likely to change temperature, a second part that is relatively unlikely to change temperature) in the face area A1 detected by the object detection means 12$b$ (step S12). Here, as shown in FIG. 8, it is assumed that the ears e1 is detected as the first part that is relatively likely to change temperature, and the forehead e2 as the second part that is relatively unlikely to change temperature change.

Next, the thermal image acquisition means 12$d$ acquires from the thermal camera 30 a thermal image (see, e.g., symbol I1 in FIG. 5) including the object taken by the thermal camera 30 (the same object as the one taken by the visible light camera 20) (step S13). Thus, a temperature distribution image of the face surface of the object is acquired.

Next, the temperature recording means 12*e* stores temperature information of the surface temperature of each part (in the thermal image I1 acquired by the thermal image acquisition means 12*d*) detected by the part detection means 12*c* in the temperature information storage unit 11*b* (step S14).

Here, it is assumed that t1*a* (see FIG. 5) as the surface temperature of the ears in an initial state and t2*a* (see FIG. 5) as the surface temperature of the forehead in an initial state are stored in the temperature information storage unit 11*b*, respectively.

Next, the notification control means 12*m* causes the notification means 50 to notify that a wind will blow from now on before the wind blowing means 40 blows the wind to the object (step S15). Specifically, the notification control means 12*m* controls the notification means 50 so as to notify that a wind will blow from now on before the wind blowing means 40 blows the wind on the object. The notification means 50 displays on the display device 51 that a wind will blow from now on, as shown in FIG. 6, before the wind blowing means 40 blows the wind to the object according to a control from the living body detection apparatus 10 (the notification control means 12*m*). In addition, audio to that effect is output from the audio output device 52.

Next, the temperature control means 12*f* controls the wind blowing means 40 (step S16). For example, the temperature control means 12*f* controls the wind blowing means 40 so as to blow a wind (for example, a cool wind) of a predetermined temperature (the temperature set by the temperature setting means 12*g*) to the object's face at a predetermined timing for a predetermined time.

The wind blowing means 40 blows a wind of a predetermined temperature to the object (the face) at a predetermined timing for a predetermined time according to a control from the living body detection apparatus 10 (the temperature control means 12*f*). The temperature control means 12*f* controls the wind blowing means 40 to stop blowing after a predetermined time has elapsed.

The wind blowing means 40 stops blowing according to the control from the living body detection apparatus 10 (the temperature control means 12*f*).

Next, the thermal image acquisition means 12*d* acquires from the thermal camera 30 a thermal image (for example, see signs 12 in FIG. 5) including the object taken by the thermal camera 30 (step S17).

Next, the temperature recording means 12*e* stores temperature information of the surface temperature of each part (in the thermal image 12 acquired by the thermal image acquisition means 12*d*) detected by the part detection means 12*c* in the temperature information storage unit 11*b* (step S18).

Here, it is assumed that t1*b* (see FIG. 5) as the surface temperature of the ears immediately after blowing the wind (for example, a cold wind) and t2*b* (see FIG. 5) as the surface temperature of the forehead immediately after blowing the wind (for example, a cold wind) are stored in the temperature information storage unit 11*b*, respectively.

Next, the object temperature change measuring means 12*h* measures a temperature change of the object (for example, the first part and the second part detected by the part detection means 12*c*) detected by the object detection means 12*b*, based on the temperature information of the surface temperature for each part stored in the temperature information storage unit 11*b* (step S19).

Here, since the surface temperatures t1*a* and t1*b* of the ears and the surface temperatures t2*a* and t2*b* of the forehead are stored in the temperature information storage unit 11*b* as the temperature information of the surface temperature of each part, the object temperature change measuring means 12*h* measures (calculates) the temperature changes t1*a*-t1*b* of the surface temperature of the ears (the first part) and the temperature changes t2*a*-t2*b* of the surface temperature of the forehead (the second part) as the temperature changes of the surface temperature of the object.

Next, the living body determination means 12*k* performs a living body determination processing to determine whether or not the object is a living body (step S20).

Next, a specific example of the living body determination processing will be described.

<Specific Example 1 of the Living Body Determination Processing>

Specific example 1 is a living body determination processing for determining whether or not the object is a living body based on a comparison result of the comparison means 12*i*.

Figure 9:
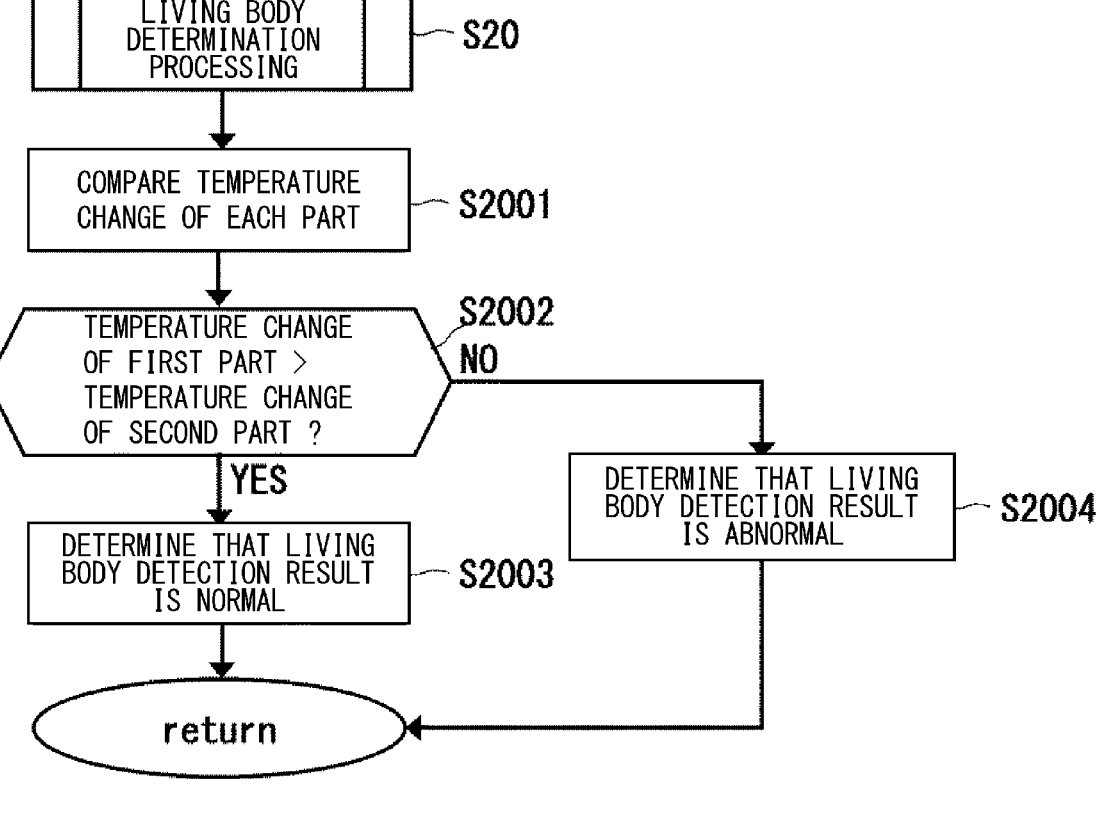
FIG. 9 is a flowchart of a specific example 1 of the living body determination processing.

FIG. 9 is a flowchart of a specific example 1 of the living body determination processing.

As shown in FIG. 9, first, the comparison means 12*i* compares the temperature change of the first part measured by the object temperature change measuring means 12*h* with the temperature change of the second part measured by the object temperature change measuring means 12*h* (step S2001).

Here, since the object temperature change measuring means 12*h* measures (calculates) the temperature changes t1*a*-t1*b* of the surface temperature of the ears (the first part) and the temperature changes t2*a*-t2*b* of the surface temperature of the forehead (the second part) as the temperature changes of the surface temperature of the object, the comparison means 12*i* compares the temperature change (t1*a*-t1*b*) of the surface temperature of the ears (the first part) with the temperature change (t2*a*-t2*b*) of the surface temperature of the forehead (the second part).

When the comparison result of the comparison means 12*i* shows the temperature change (for example, t1*a*-t1*b*) of the surface temperature of the first part (the ears, for example) >the temperature change (t2*a*-t2*b*) of the surface temperature of the second part (for example, the forehead) (step S2002: YES), the living body determination means 12*k* determines that the living body detection result is normal, that is, the object is a living body (step S2003).

On the other hand, when the comparison result of the comparison means 12*i* does not show the temperature change (for example, t1*a*-t1*b*) of the surface temperature of the first part (the ears, for example)>the temperature change (t2*a*-t2*b*) of the surface temperature of the second part (for example, the forehead) (step S2002: NO), the living body determination means 12*k* determines that the living body detection result is abnormal, that is, the object is not a living body (step S2004).

<Specific Example 2 of the Living Body Determination Processing>

Specific example 2 is a living body determination processing for determining whether or not the object is a living body based on a determination result of the temperature return determination means 12*j*.

Figure 10:
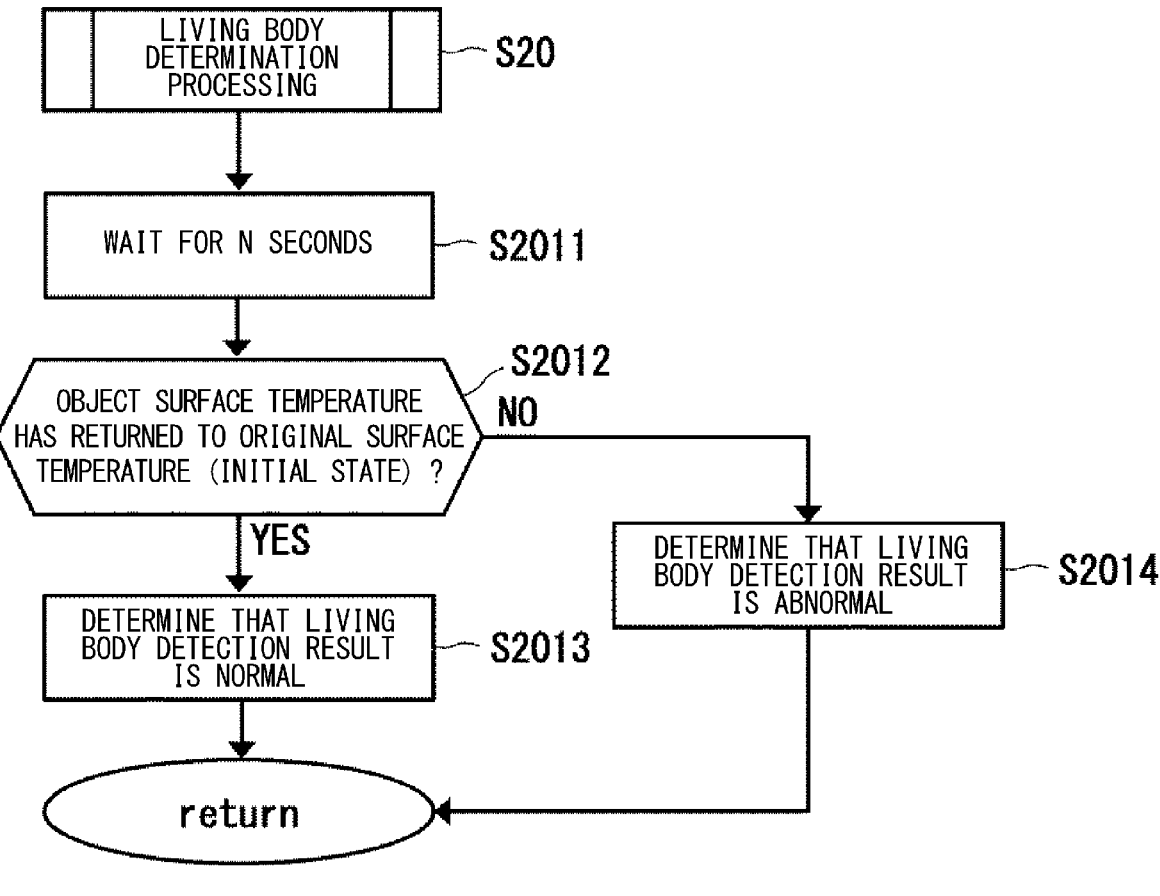
FIG. 10 is a flowchart of specific example 2 of the living body determination processing.

FIG. 10 is a flowchart of specific example 2 of the living body determination processing.

First, after the wind blowing means 40 stops blowing a wind, it waits for N seconds as shown in FIG. 10 (step S2011). N seconds is a number of seconds considered so that a surface temperature of the object is a surface temperature before the change, e.g., 10 seconds.

Next, the temperature return determination means $12j$ determines whether or not the object surface temperature has returned to an original surface temperature (an initial state) before the change (step S2012).

As a result, when it is determined that the object surface temperature has returned to the original surface temperature (the initial state) (step S2012: YES), the living body determination means $12k$ determines that the living body detection result is normal, that is, the object is a living body (step S2013).

On the other hand, when it is determined that the object surface temperature has not returned to the original surface temperature (the initial state) (step S2012: NO), the living body determination means $12k$ determines that the living body detection result is abnormal, that is, the object is not a living body (step S2014).

<Specific Example 3 of the Living Body Determination Processing>

Specific example 3 is a living body determination processing combining specific example 1 and specific example 2. According to specific example 3, the accuracy of the living body determination can be improved over specific example 1 and specific example 2.

Figure 11:
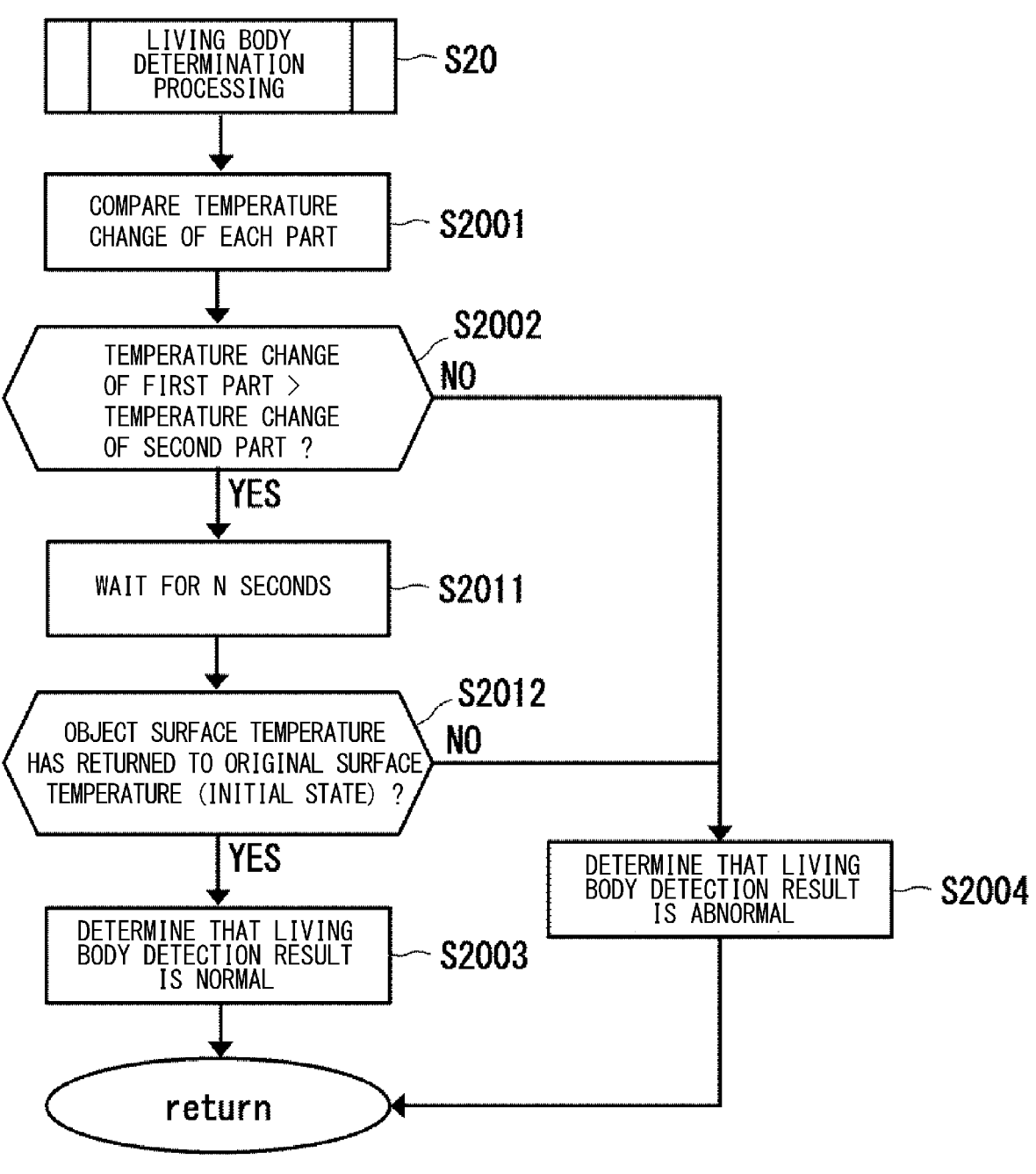
FIG. 11 is a flowchart of specific example 3 of the living body determination processing.

FIG. 11 is a flowchart of specific example 3 of the living body determination processing.

Since each step in FIG. 11 is similar to those in FIG. 9 and FIG. 10, its explanation is omitted.

<Specific Example 4 of the Living Body Determination Processing>

Figure 12:
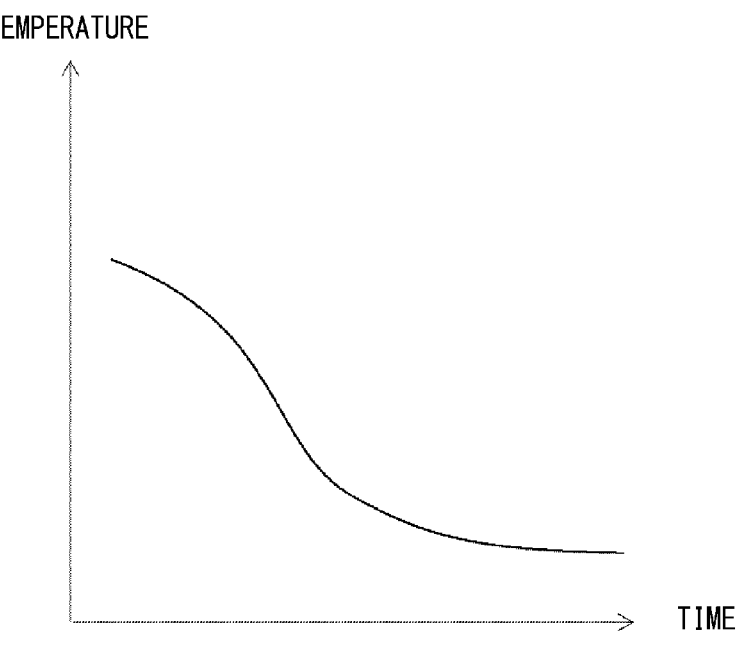
FIG. 12 shows an example of a temperature change pattern unique to a living body.

When the object is a living body, a surface temperature of the object is considered to change in a pattern unique to the living body, as shown in FIG. 12, for example. FIG. 12 shows an example of a temperature change pattern unique to a living body.

Therefore, in specific example 4, it is determined whether or not the object is a living body by comparing a change pattern of a surface temperature of the object with a change pattern of a surface temperature of a reference person.

Figure 13:
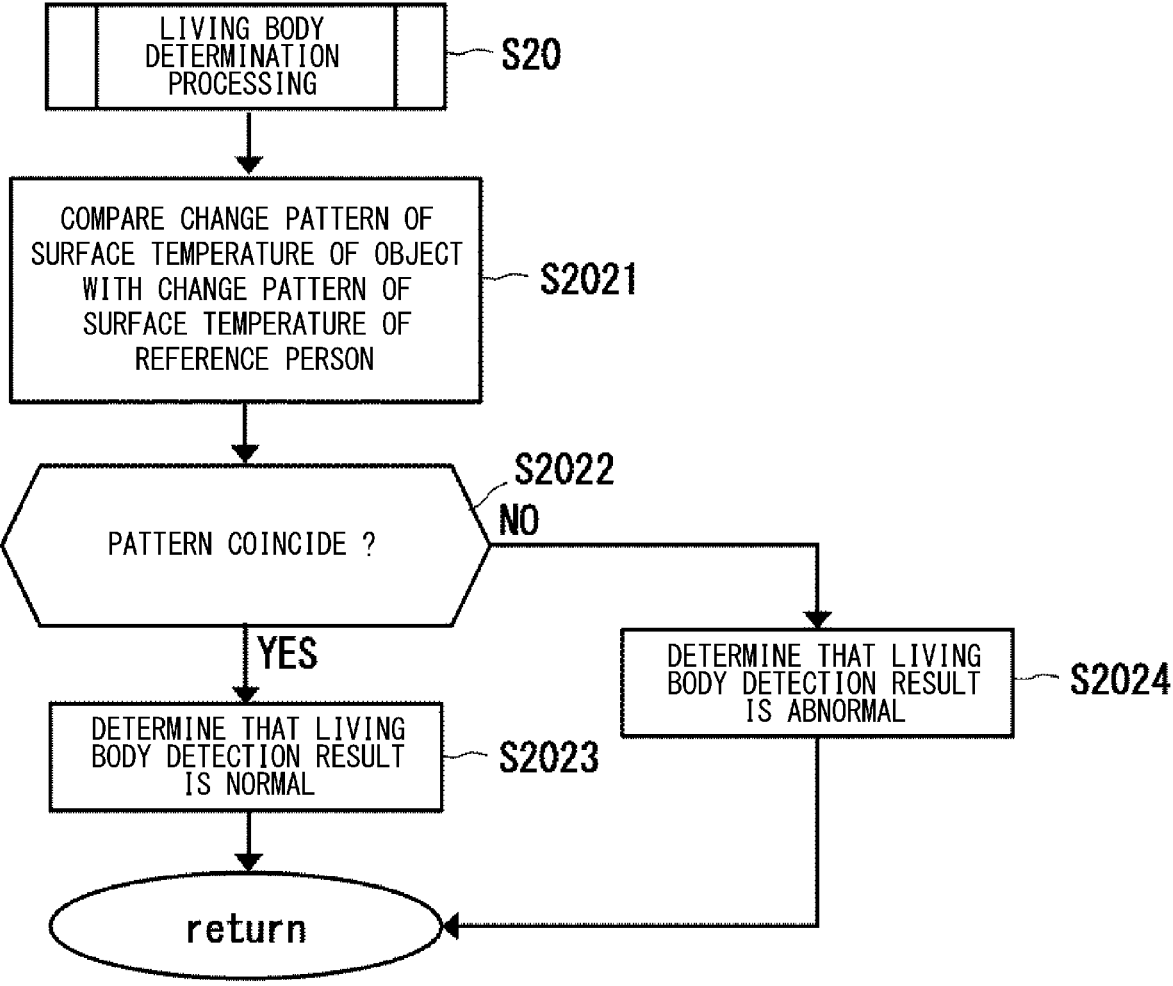
FIG. 13 is a flowchart of specific example 4 of living body determination processing.

FIG. 13 is a flowchart of specific example 4 of living body determination processing.

As shown in FIG. 13, first, the comparison means $12i$ compares a change pattern of a surface temperature of the object with a change pattern of a surface temperature of a reference person (step S2021). As the change pattern of the surface temperature of the object, for example, one stored in the temperature information storage unit $11b$ is used. As the change pattern of the surface temperature of the reference person, for example, one stored in the storage unit 11 is used.

As a result of the comparison in step S2021, when the change pattern of the surface temperature of the object and the change pattern of the surface temperature of the reference person coincide (or roughly coincide) (step S2022: YES), the living body determination means $12k$ determines that the living body detection result is normal, that is, the object is a living body (step S2023).

On the other hand, as a result of the comparison in step S2021, when the change pattern of the surface temperature of the object and the change pattern of the surface temperature of the reference person does not coincide (or roughly coincide) (step S2022: NO), the living body determination means $12k$ determines that the living body detection result is abnormal, that is, the object is not a living body (step S2024).

Note that specific examples 1-4 of the above the living body determination processing may be used in combination as appropriate.

Next, return to FIG. 7 and continue the explanation.

When the determination result of the living body determination processing (step S20) is living body detection results normal (step S21: YES), a face authentication of the object is performed (step S22). For example, the authentication control means $12n$ causes the authentication apparatus 60 to perform the face authentication of the object by sending a face authentication request containing a face image (a visible image) of the object to the authentication apparatus 60. Note that the authentication result (the collation result) is notified to the entrance/exit management system 70.

On the other hand, when the determination result of the living body determination processing (step S20) is living body detection results abnormal (step S21: NO), the processing is terminated without performing the face authentication of the object (step S21: NO).

The living body determination means $12k$ may determine whether or not the object is a living body by considering further additional conditions in addition to the specific example 1-4 of the above the living body determination processing.

Next, specific examples of additional conditions considered by the living body determination means $12k$ will be described.

<Specific Example 1 of the Additional Condition>

The living body determination means $12k$ may determine whether or not the object is a living body considering a result of comparison between a change pattern of a surface temperature of the object and a change pattern of a surface temperature of a reference non-person. The reference non-person means, for example, anything other than a person (a living body), such as a tablet on which a photograph (or video) is displayed, or a paper photograph of a person. The change pattern of the surface temperature of the reference non-person is, for example, a change pattern of a surface temperature of a tablet on which a photograph (or video) is displayed, a change pattern of a paper photograph of a person (non-living body). The change pattern of the surface temperature of the reference non-person shows a temperature change when a wind is blown on the tablet or the photograph.

<Specific Example 2 of the Additional Condition>

The living body determination means $12k$ may determine whether or not the object is a living body considering a reaction of the object (for example, close eyes, open mouth) when the wind blowing means 40 blows a wind to the object.

An example of this reaction determination processing is described below.

The following processing is performed by the control unit 12 (a processor) executing a program read from the program storage unit $11a$ into a RAM (not shown).

Figure 23:
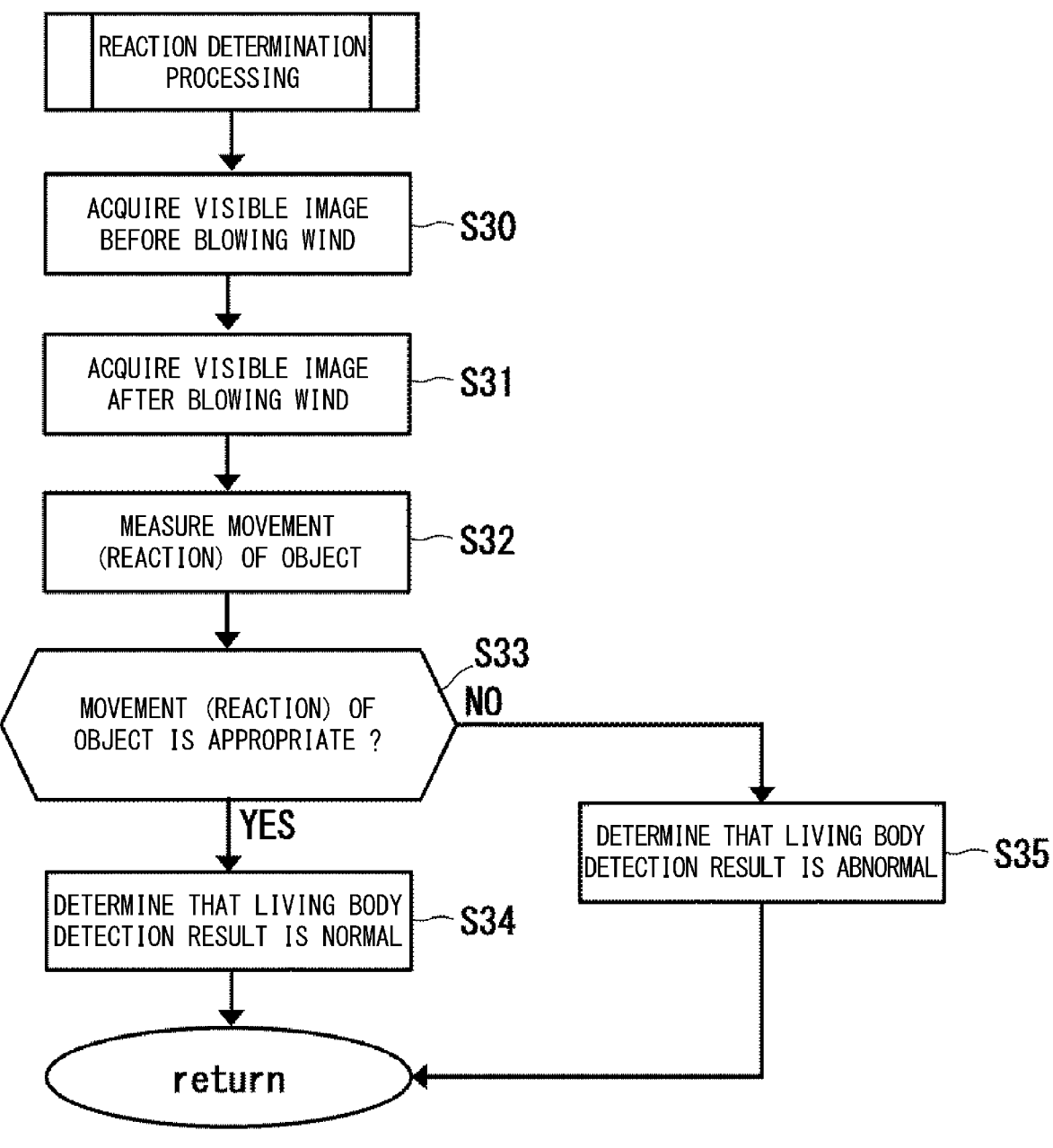
FIG. 23 is a flowchart of an example of the reaction determination processing.

FIG. 23 is a flowchart of an example of the reaction determination processing.

The reaction determination processing shown in FIG. 23 is executed in parallel with, for example, the processing shown in FIG. 7.

First, the visible image acquisition means $12a$ acquires a visible image including the object before the wind blowing means 40 blows a wind to the object (step S30).

Next, the visible image acquisition means $12a$ acquires a visible image including the object after the wind blowing means 40 blows the wind to the object (step S31).

Next, a movement (a reaction) of the object is measured by analyzing the visible image before blowing the wind acquired in step S30 and the visible image after blowing the wind acquired in step S31 (step S32).

Next, it is determined whether or not the movement of the object measured in step S32 is appropriate (step S33). For example, it is determined whether or not an appropriate reaction has been performed according to the position to which the wind is blown by the wind blowing means 40.

As a result, when it is determined that the appropriate reaction has been performed (step S33: YES), for example, when the right side of the object's face is blown with the wind and the object closes the right eye, it is determined that the living body detection result is normal, that is, the object is a living body (step S34).

On the other hand, when it is determined that the appropriate reaction has not been performed (step S33: NO), for example, when the right side of the object's face is blown with the wind and the object closes the left eye, it is determined that the living body detection result is abnormal, that is, the object is not a living body (step S35).

<Specific Example 3 of the Additional Condition>

The living body determination means 12k may determine whether or not the object is a living body considering a surface condition (for example, a color of a surface, a pores tightness) of the object before and after changing a surface temperature. Note that the surface condition of the object can be determined from the difference between the visible image taken before the wind blowing means 40 blows a wind to the object and the visible image taken after the wind blowing means 40 blows the wind to the object.

<Specific Example 4 of the Additional Condition>

When the object is a tablet on which a photograph (or video) of a person is displayed or a paper photograph of a person, the living body determination means 12k may determine whether or not the object is a living body considering a temperature change in a background of the object, because the temperature change pattern in the background of the object is different from that in the case of a person (a living body).

In the living body detection apparatus described in the above patent literature 1, for example, when an elaborate 3D mask or a life-size mask using a photograph with the eyes and mouth cut out is worn, a disguisement (for example, impersonation during face authentication) is difficult to detect, because the 3D mask and the mask are three-dimensional, with eyes and mouths cut out to expose the living body of a wearer.

On the other hand, according to the second embodiment, a disguisement using an elaborate 3D mask or a disguisement (for example, impersonation during face authentication) using a life-size mask using a photograph with the eyes and mouth cut out can be detected.

This is because whether or not the object is a living body is determined based on the temperature change of the surface (for example, the face) temperature of the object, not the surface (for example, the face) temperature of the object.

In addition, according to the second embodiment, a disguisement (for example, impersonation during a face authentication) by a person (other than a living person) in a photograph (or video) displayed on a display of a tablet, etc., or a person (other than a living person) in a paper photograph can also be detected.

This is also because whether or not the object is a living body is determined based on the temperature change of the surface (for example, the face) temperature of the object, not the surface (for example, the face) temperature of the object.

According to the second embodiment, the temperature change of the object (the part) detected from the visible image can be measured based on the thermal image.

In addition, according to the second embodiment, it is possible to determine whether or not the object is a living body based on the temperature change of the part of the object. At that time, the accuracy of the living body detection can be improved by selecting, as the part of the object, for example, a part with living body unique temperature-changing characteristics.

In addition, according to the second embodiment, the accuracy of living body detection can be improved by selecting the first part that is relatively likely to change temperature and the second part that is relatively unlikely to change temperature as the part of the object and comparing the temperature change of the first part with the temperature change of the second part.

In addition, according to the second embodiment, the accuracy of the living body detection can be improved by determining whether or not the surface temperature of the object (the part) has returned to the original surface temperature before the change.

In addition, according to the second embodiment, the accuracy of the living body detection can be improved by comparing the change pattern of the surface temperature of the object (at least one part) with the change pattern of the surface temperature of the reference person.

In addition, according to the second embodiment, the surface temperature of the object (the part) can be quickly changed by using the surface temperature change means (wind blowing means) that changes the surface temperature of the object (the part). As a result, the time required for living body detection can be reduced.

In addition, according to the second embodiment, since the temperature setting means for setting the predetermined temperature is provided, the wind of the predetermined temperature thus setting can be blown to the object.

In addition, according to the second embodiment, since the notification means notifies that a wind will blow from now on before blowing the wind to the object (for example, the face), it is possible to suppress giving discomfort to the object.

In addition, according to the second embodiment, the accuracy of the living body detection can be improved by determining whether or not the object is a living body considering the result of comparison between the change pattern of the surface temperature of the object (the part) and the change pattern of the surface temperature of the reference non-person.

In addition, according to the second embodiment, the accuracy of the living body detection can be improved by determining whether or not the object is a living body considering the reaction of the object when the wind blows to the object.

In addition, according to the second embodiment, the accuracy of the living body detection can be improved by determining whether or not the object is a living body considering the surface condition of the object before and after changing the surface temperature.

In addition, according to the second embodiment, the accuracy of the living body detection can be improved by determining whether or not the object is a living body considering the temperature change in the background of the object.

In addition, according to the second embodiment, since the authentication apparatus 60 performs the face authentication of the object after the living body determination means determines that the object is a living body, it is possible to suppress the execution of the face authentication by the elaborate 3D mask, the face authentication by the life-size mask using a photograph with the eyes and mouth cut out, the face authentication by a person (non-living body) in a photograph (or video) displayed on a display such as a tablet, the face authentication by a person (non-living body) in a paper photograph.

Next, variations are described.

First, a variation of the wind blowing means 40 will be described.

Figure 22:
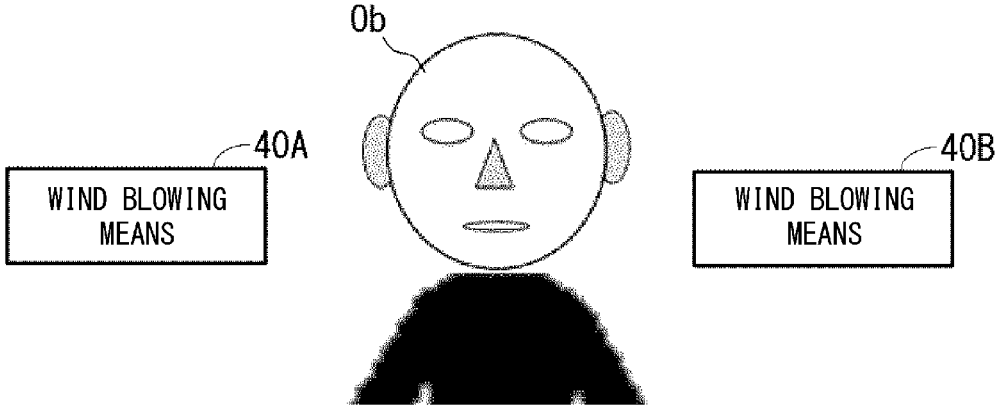
FIG. 22 is a schematic configuration diagram of a variation of the wind blowing means 40.

FIG. 22 is a schematic configuration diagram of a variation of the wind blowing means 40.

In the above second embodiment, an example using one wind blowing means 40 was described in step S15 (see FIG. 7), but it is not limited to this, as shown in FIG. 22, multiple wind blowing means 40A and 40B may be used.

At that time, regarding the arrangement of one wind blowing means 40A and the other wind blowing means 40B, for example, as shown in FIG. 22, one wind blowing means 40A may be arranged to blow a wind to the left half of the face of the object Ob (the left half in FIG. 22) and the other wind blowing means 40B may be arranged to blow a wind to the right half of the face of the object Ob (the right half in FIG. 22). Although not shown, one wind blowing means 40A may be arranged to blow a wind to the upper half of the face of the object Ob, and the other wind blowing means 40B may be arranged to blow a wind to the lower half of the face of the object Ob, or may be arranged in various other forms.

The temperature of the wind blown by one wind blowing means 40A and the temperature of the wind blown by the other wind blowing means 40B may be the same or different from each other. For example, in step S15 (see FIG. 7), one wind blowing means 40A may blow a warm wind and the other wind blowing means 40B may blow a cold wind. The strength of the wind blown by one wind blowing means 40A and the strength of the wind blown by the other wind blowing means 40B may be the same or different from each other.

The timing of blowing by one wind blowing means 40A and the timing of blowing by the other wind blowing means 40B may be the same or different from each other. In addition, one wind blowing means 40A and the other wind blowing means 40B may continue blowing wind all the time, respectively. In addition, one wind blowing means 40A and the other wind blowing means 40B may blow a wind continuously or intermittently, respectively.

The wind blowing means 40 are not limited to the wind blowing means 40A and 40B, but may be 3 or more.

Next, a living body detection system 1A are described in detail as a third embodiment of this disclosure.

Figure 14:
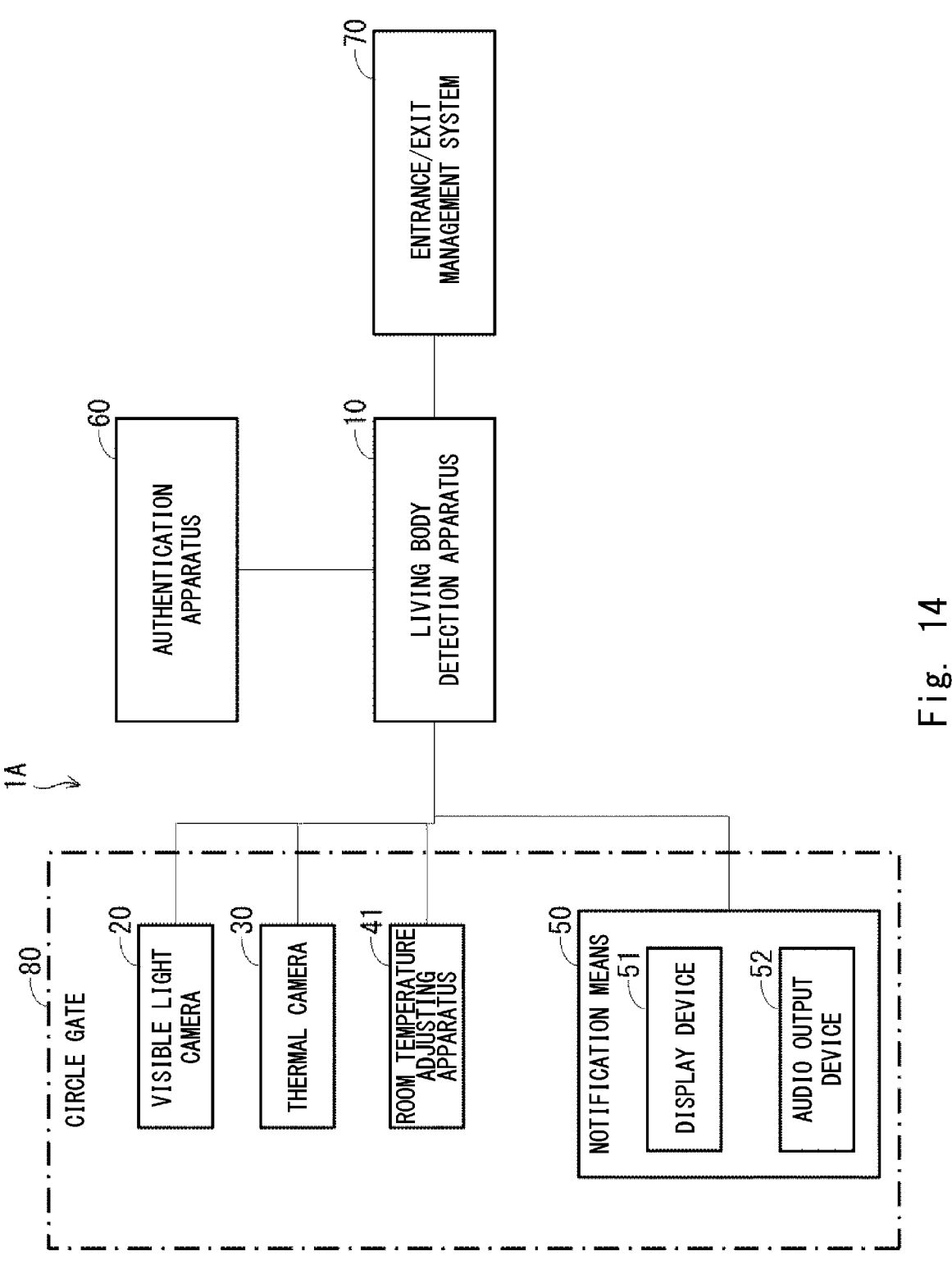
FIG. 14 is a block diagram showing the configuration of the living body detection system 1A according to the third embodiment.

FIG. 14 is a block diagram showing the configuration of the living body detection system 1A according to the third embodiment.

Hereafter, the differences from the second embodiment will be mainly explained, and the same components will be denoted by the same symbols, and the explanation will be omitted as appropriate.

As shown in FIG. 14, the living body detection system 1A according to the third embodiment is comprises a circle gate having a space isolated from the outside. The space isolated from the outside may be provided other than the circle gate.

Figure 15:
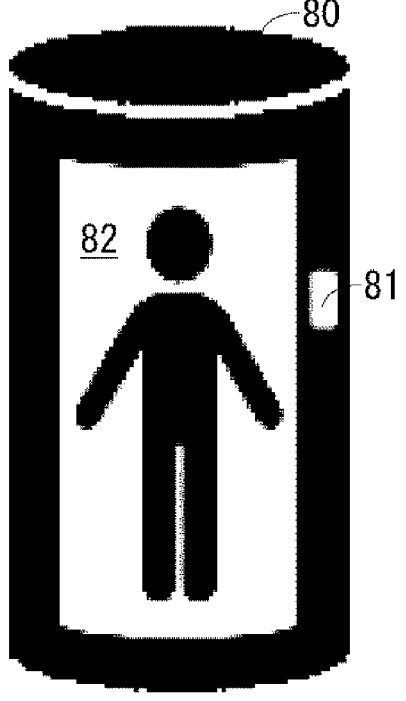
FIG. 15 shows an example of a circle gate 80.

FIG. 15 shows an example of a circle gate 80.

Figure 16:
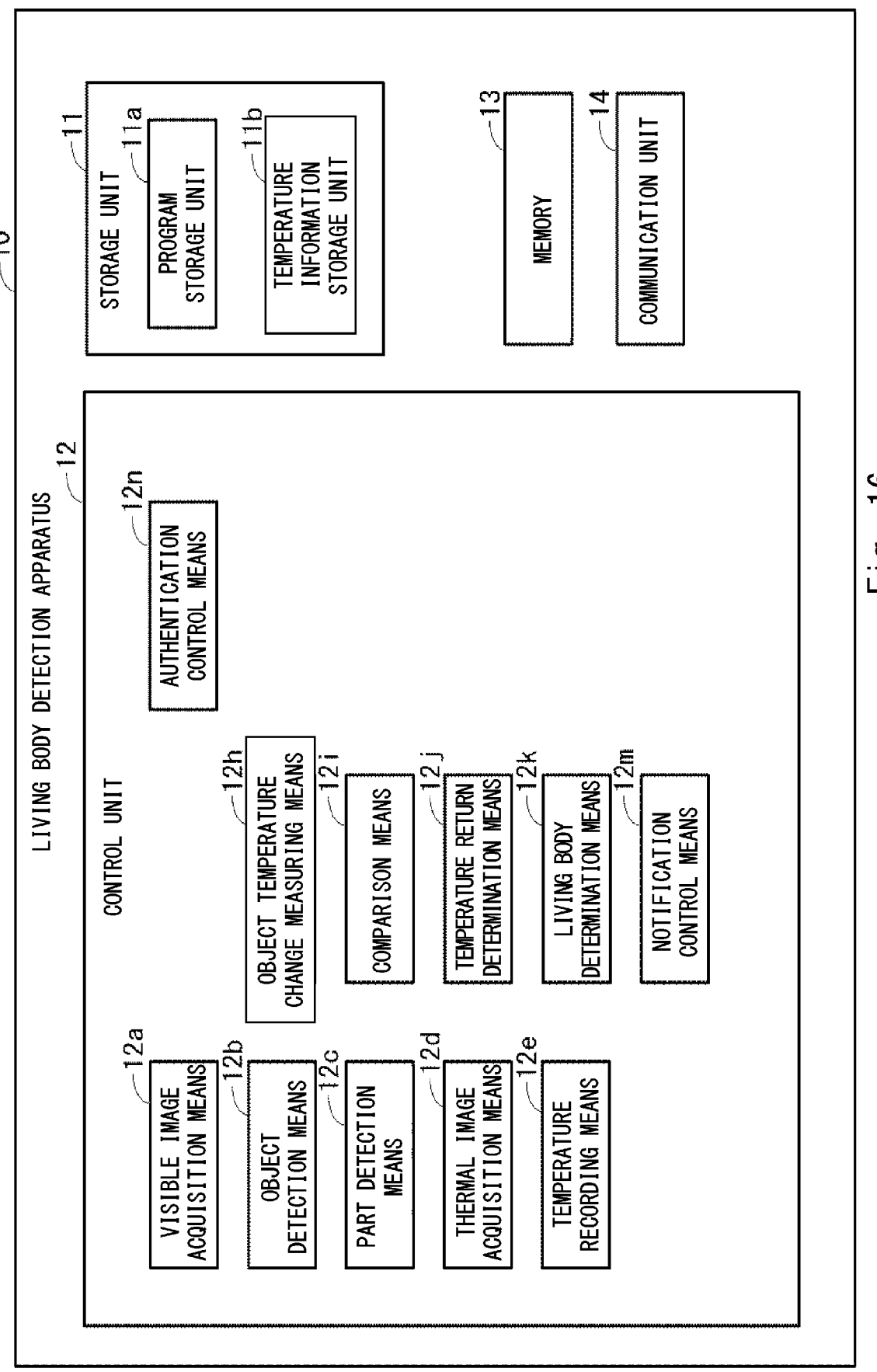
FIG. 16 is a block diagram showing the configuration of the living body detection apparatus 10 according to the third embodiment.

As shown in FIG. 15, the circle gate 80 has a door 81 that can be opened and closed by an object Ob and a space 82 that can accommodate the object Ob. The visible light camera 20, the thermal camera 30, and the notification means 50 are installed in the space 82 of the circle gate 80. A room temperature adjusting apparatus 41 (an air conditioner, etc.) is installed in the space 82 of the circle gate 80. The room temperature adjusting apparatus 41 is another example of surface temperature change means in this disclosure. As shown in FIG. 16, the temperature control means 12$f$ and the temperature setting means 12$g$ are omitted. FIG. 16 is a block diagram showing the configuration of the living body detection apparatus 10 according to the third embodiment.

Next, an example of the operation of the living body detection apparatus 10 according to the third embodiment will be described.

Figure 17:
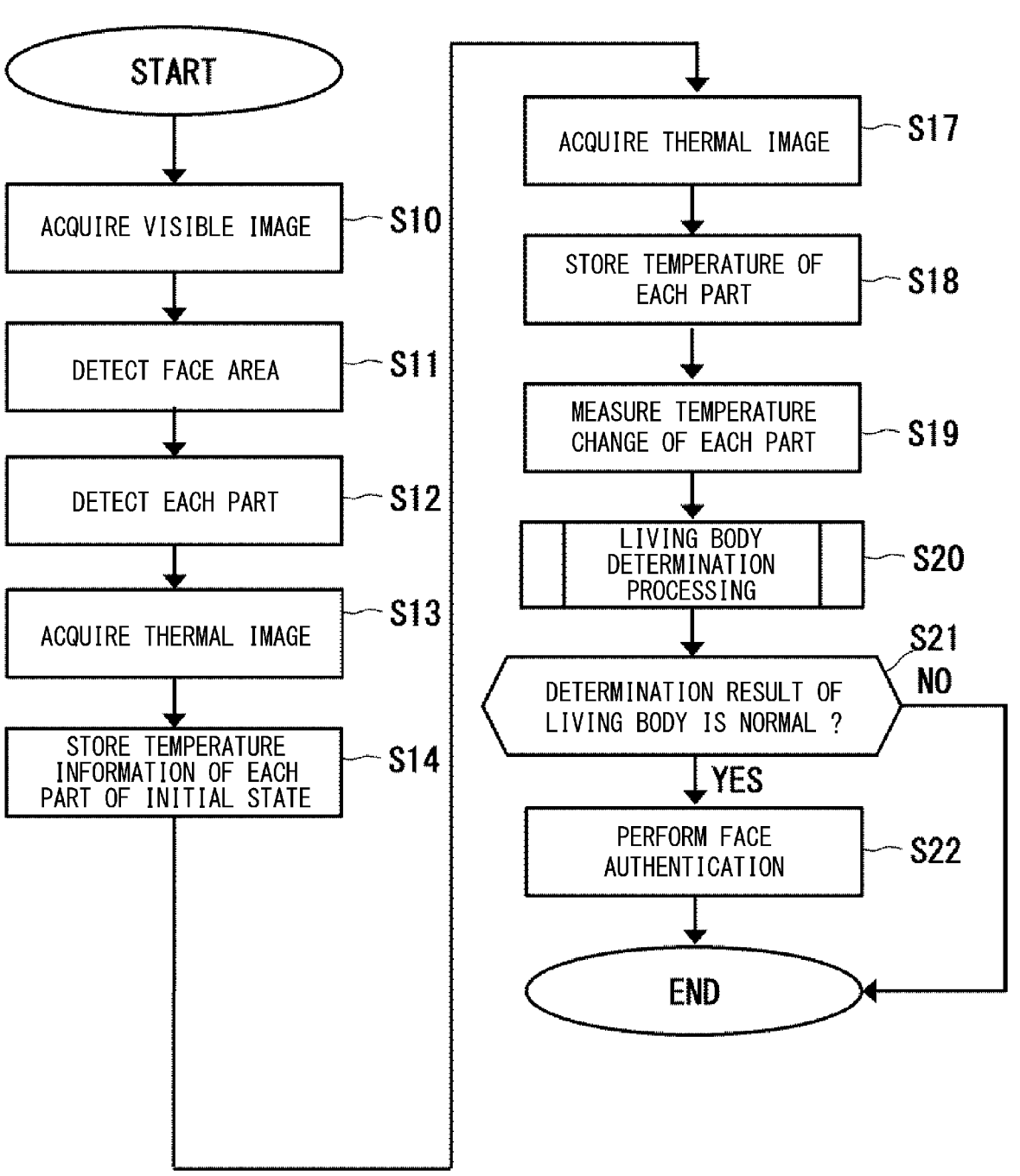
FIG. 17 is a flowchart of one example of the operation of the living body detection apparatus 10 according to the third embodiment.

FIG. 17 is a flowchart of one example of the operation of the living body detection apparatus 10 according to the third embodiment. FIG. 17 is similar to FIG. 7 except that steps S15 and S16 are omitted.

The processing in FIG. 16 is performed in a state where the object Ob opens the door 81, stands or sits, and is housed in the space 82 of the circle gate 80. At that time, the space 82 of the circle gate 80 is setting lower (or higher) than the ambient temperature outside the space 82 of the circle gate 80 by the room temperature adjusting apparatus 41 (an air conditioner, etc.).

The same effect as the second embodiment can be achieved by the third embodiment.

In addition, according to the third embodiment, since the room temperature adjusting apparatus 41 installed in the space 82 isolated from the outside is used as the surface temperature change means for changing the surface temperature of the object, the surface temperature of the object (the part) can be changed without using the wind blowing means 40.

Next, variations of the second and third embodiment will be described.

In the above second embodiment and the third embodiment, an example using the wind blowing means and the room temperature adjusting apparatus as the surface temperature change means for changing the surface temperature of the object was described, but it is not limited to this.

For example, the surface temperature change means (the wind blowing means and the room temperature adjusting apparatus) for changing the surface temperature of the object may be omitted.

In this case, for example, the notification control means 12$m$ causes the notification means 50 to notify the object of the content that urges an action to be taken to change the body temperature before the object temperature change measuring means 12$h$ measures the temperature change of the surface temperature of the object (before step S19 in FIG. 7, FIG. 17). Specifically, the notification control means 12$m$ controls the notification means 50 so as to notify the object of the content that urges an action to be taken to change the body temperature before the object temperature change measuring means 12$h$ measures the temperature change of the surface temperature of the object (before step S19 in FIG. 7, FIG. 17).

Figure 18:
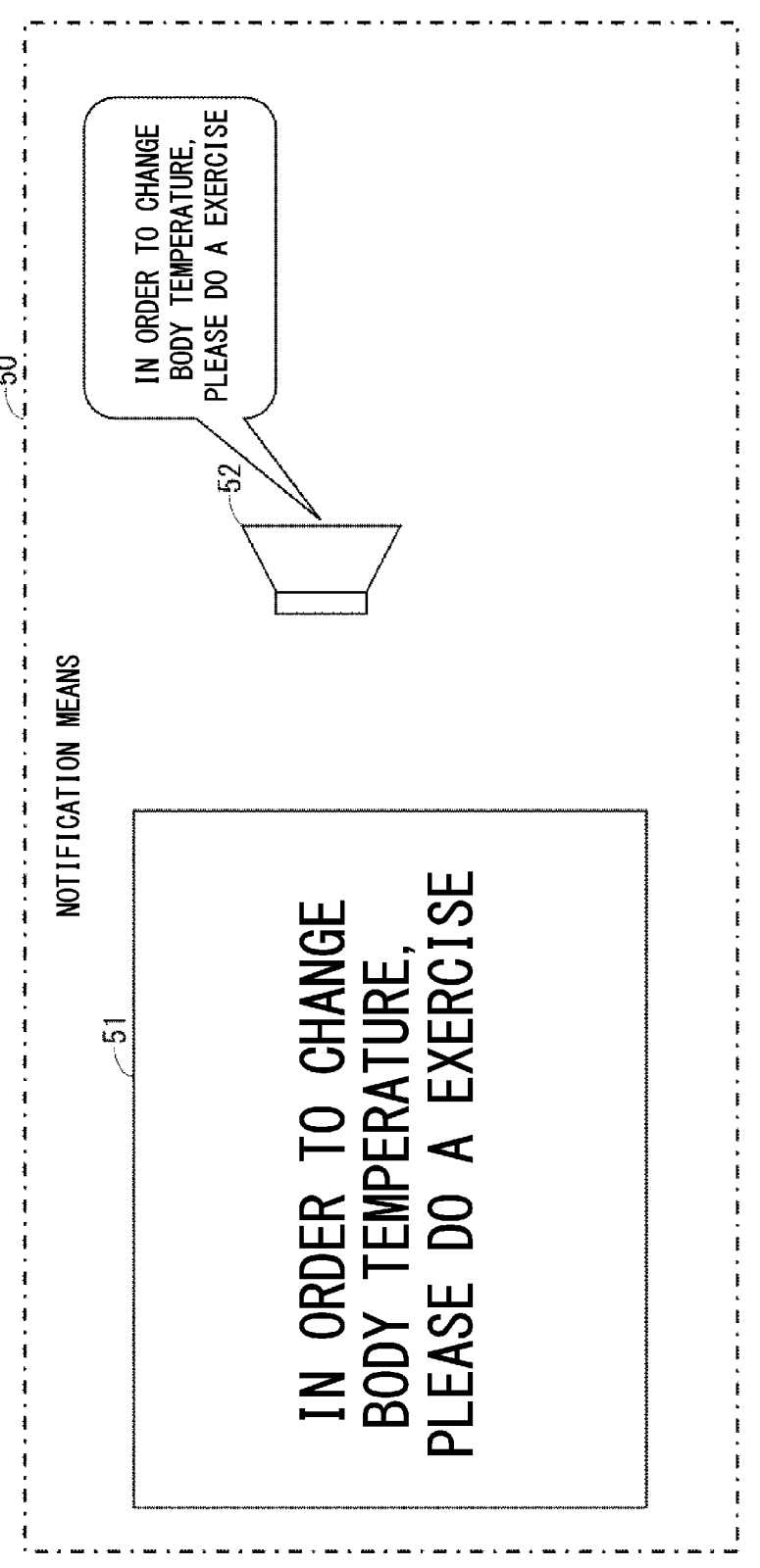
FIG. 18 shows another example of the contents notified by the notification means 50.

According to the control from the living body detection apparatus 10 (the notification control means 12$m$), the notification means 50 displays on the display device 51 the content that urges an action to be taken to change the body temperature, for example, as shown in FIG. 18, before the object temperature change measuring means 12$h$ measures the temperature change of the surface temperature of the object (before step S19 in FIG. 7, FIG. 17). In addition, audio to that effect is output from the audio output device 52. FIG. 18 shows another example of the contents notified by the notification means 50.

According to this modified example, the same effect as in the second embodiment can be achieved.

In addition, according to this modified example, by notifying the content that urges an action to be taken to change the body temperature, the surface temperature of the object (the part) can be changed without using the surface temperature changing means such as the wind blowing means or the room temperature adjusting apparatus.

Next, a living body detection system 1B is described in detail as a fourth embodiment of this disclosure.

Figure 19:
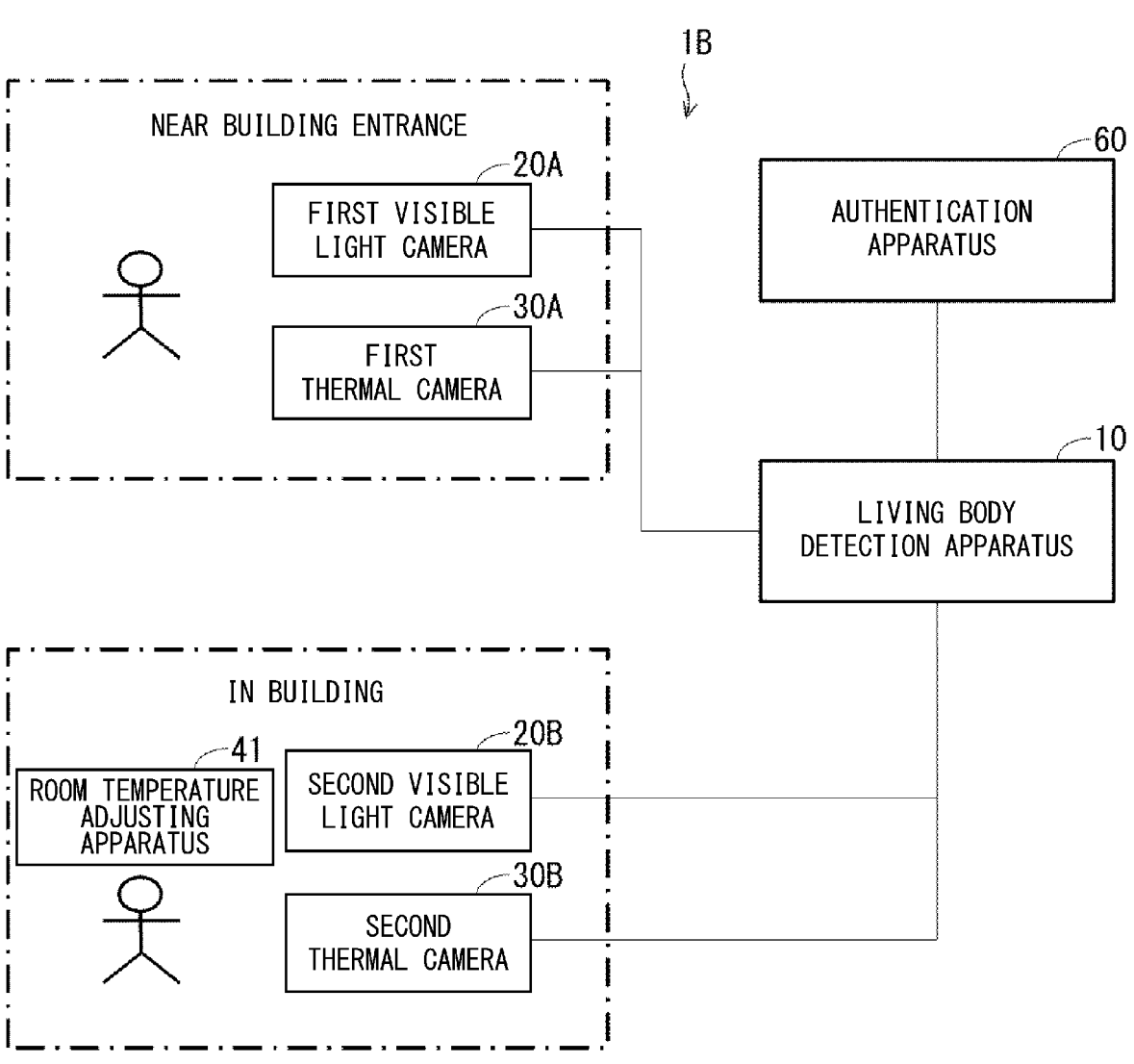
FIG. 19 is a block diagram showing the configuration of the living body detection system 1B according to the fourth embodiment.

FIG. 19 is a block diagram showing the configuration of the living body detection system 1B according to the fourth embodiment.

Hereafter, the differences from the second embodiment will be mainly explained, and the same components will be denoted by the same symbols, and the explanation will be omitted as appropriate.

As shown in FIG. 19, the living body detection system 1B according to the fourth embodiment comprise a first visible light camera 20A, a second visible light camera 20B, a first thermal camera 30A, and a second thermal camera 30B. In the fourth embodiment, the flapper gate and the entrance/exit management system 70 are omitted.

Figure 20:
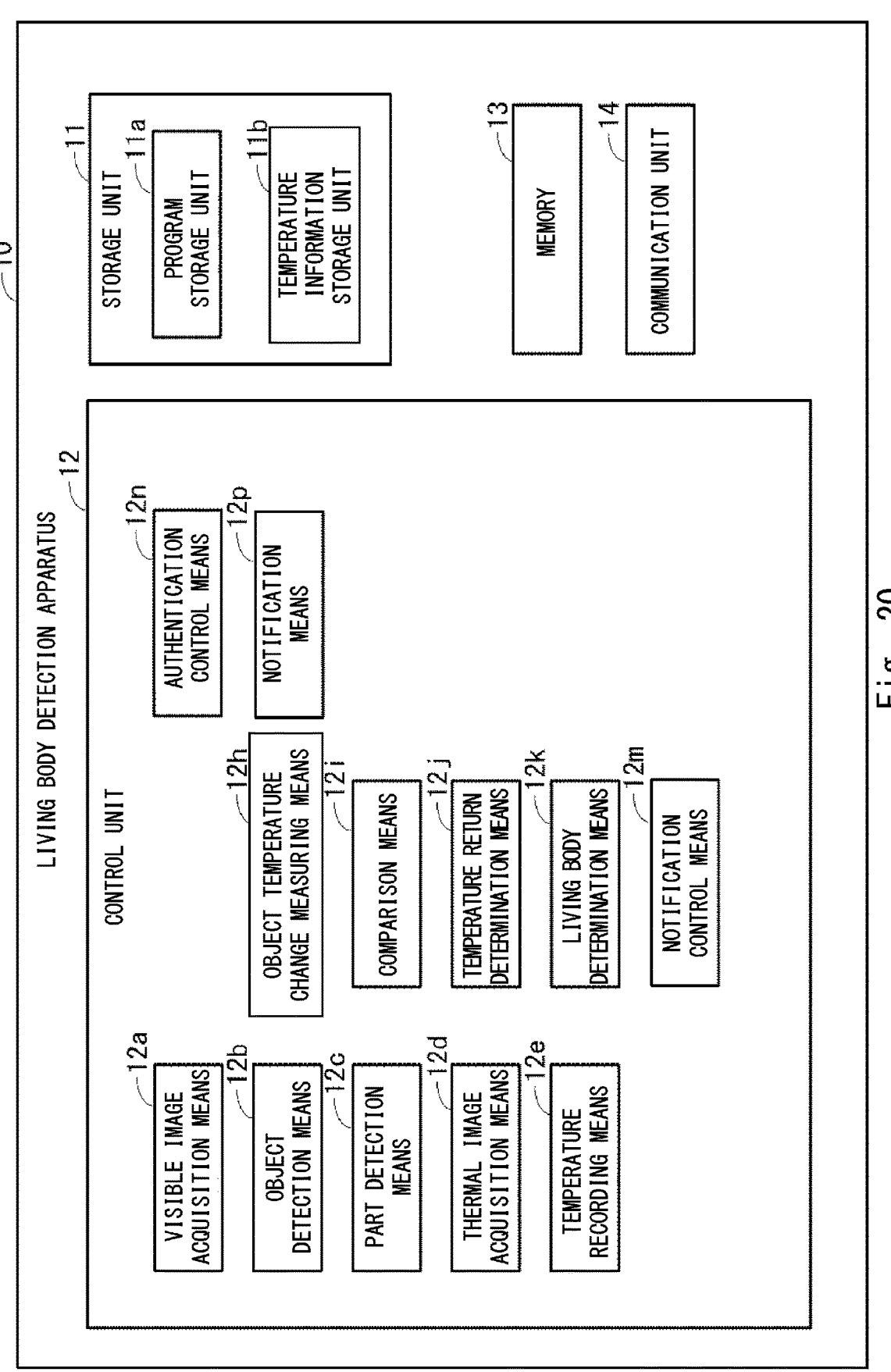
FIG. 20 is a block diagram showing the configuration of the living body detection apparatus 10 according to the fourth embodiment.

The first visible light camera 20A and the first thermal camera 30A are installed near an entrance of a building, for example. The second visible light camera 20B and the second thermal camera 30B are installed in the building. The room temperature adjusting apparatus 41 (an air conditioner, etc.) is installed in the building. The room temperature adjusting apparatus 41 is an example of the surface temperature change means in this disclosure. As shown in FIG. 20, the temperature control means 12f and the temperature setting means 12g are omitted. FIG. 20 is a block diagram showing the configuration of the living body detection apparatus 10 according to the fourth embodiment. A notification means 12p has also been added. When the living body determination means 12k determines that the object is not a living body, the notification means 12p notifies the fact.

Next, an example of the operation of the living body detection apparatus 10 according to the fourth embodiment will be described.

Figure 21:
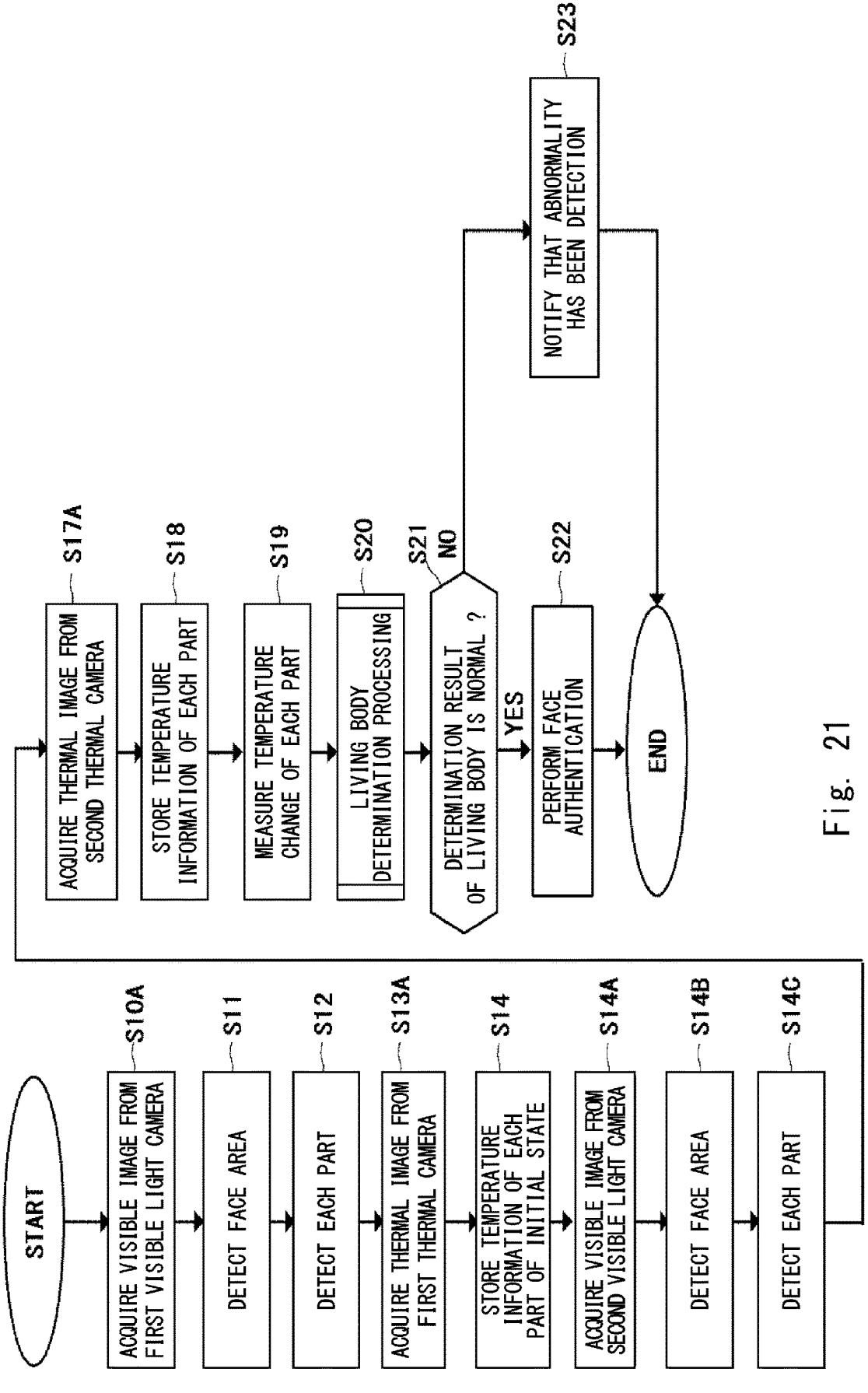
FIG. 21 is a flowchart of one example of the operation of the living body detection apparatus 10 according to the fourth embodiment.

FIG. 21 is a flowchart of one example of the operation of the living body detection apparatus 10 according to the fourth embodiment.

The following processing is realized by the control unit 12 (a processor) executing a program read from the program storage unit 11a into a RAM (not shown).

First, the visible image acquisition means 12a acquires a visible image including an object taken by the first visible light camera 20A from the first visible light camera 20A installed near the entrance of the building (step S10A). Here, it is assumed that the visible image I including the face of the object Ob shown in FIG. 8 is acquired.

Next, the object detection means 12b detects the face area A1 of the object Ob in the visible image I acquired by the visible image acquisition means 12a (step S11).

Next, the part detection means 12c detects each part (a first part that is relatively likely to change temperature, a second part that is relatively unlikely to change temperature) in the face area A1 detected by the object detection means 12b (step S12). Here, as shown in FIG. 8, it is assumed that the ears e1 is detected as the first part that is relatively likely to change temperature, and the forehead e2 as the second part that is relatively unlikely to change temperature change.

Next, the thermal image acquisition means 12d acquires from the first thermal camera 30A a thermal image (see, e.g., symbol I1 in FIG. 5) including the object taken by the first thermal camera 30A (the same object as the one taken by the first visible light camera 20A) installed near the entrance of the building (step S13A).

Next, the temperature recording means 12e stores temperature information of the surface temperature of each part (in the thermal image I1 acquired by the thermal image acquisition means 12d) detected by the part detection means 12c in the temperature information storage unit 11b (step S14).

Here, it is assumed that t1a (see FIG. 5) as the surface temperature of the ears in the initial state and t2a (see FIG. 5) as the surface temperature of the forehead in the initial state are stored in the temperature information storage unit 11b, respectively.

Next, the visible image acquisition means 12a acquires a visible image including the object taken by the second visible light camera 20B from the second visible light camera 20B installed in the building as in step S10A (step S14A).

Next, the object detection means 12b detects the face area of the object Ob in the visible image acquired by the visible image acquisition means 12a as in step S11 (step S14B).

Next, the part detection means 12c detects the part (the first part that is relatively likely to change temperature, the second part that is relatively unlikely to change temperature) in the face area detected by the object detection means 12b as in step S12 (step S14C).

Next, the thermal image acquisition means 12d acquires from the second thermal camera 30B a thermal image (see, e.g., symbol I2 in FIG. 5) including the object taken by the second thermal camera 30B installed in the building (step S17A).

Next, the temperature recording means 12e stores temperature information of the surface temperature of each part (in the thermal image I2 acquired by the thermal image acquisition means 12d) detected by the part detection means 12c in the temperature information storage unit 11b (step S18).

Here, it is assumed that t1b (see FIG. 5) as the surface temperature of the ears immediately after blowing the wind (for example, a cold wind) and t2b (see FIG. 5) as the surface temperature of the forehead immediately after blowing the wind (for example, a cold wind) are stored in the temperature information storage unit 11b, respectively.

Next, the object temperature change measuring means 12h measures a temperature change of the object (for example, the first part and the second part detected by the part detection means 12c) detected by the object detection means 12b, based on the temperature information of the surface temperature for each part stored in the temperature information storage unit 11b (step S19).

Here, since the surface temperatures t1a and t1b of the ears and the surface temperatures t2a and t2b of the forehead are stored in the temperature information storage unit 11b as the temperature information of the surface temperature of each part, the object temperature change measuring means 12h measures (calculates) the temperature changes t1a-t1b of the surface temperature of the ears (the first part) and the temperature changes t2a-t2b of the surface temperature of the forehead (the second part) as the temperature changes of the surface temperature of the object.

Next, the living body determination means 12k performs a living body determination processing to determine whether or not the object is a living body (step S20). Since a specific example of this living body determination processing has already been described, its explanation is omitted.

When the determination result of the living body determination processing (step S20) is living body detection results normal (step S21: YES), a face authentication of the object is performed (step S22).

For example, the authentication control means 12$n$ causes the authentication apparatus 60 for performing authentication to perform the face authentication of the object by sending a face authentication request containing a face image (a visible image) of the object to the authentication apparatus 60 for performing face authentication. The authentication result (collation result) is notified to the entrance/exit management system 70.

On the other hand, when the determination result of the living body determination processing (step S20) is living body detection results abnormal (step S21: NO), the notification means 12$p$ notifies that an abnormality has been detection (step S23). For example, in order to display the fact that the abnormality has been detection on the monitor or the like, which is visually observed by a guard or a watchman, the notification means 12$p$ notifies the fact that the abnormality has been detection on the predetermined apparatus via the communication unit 14. At that time, the location information of the object whose abnormality has been detection may also be notified.

The same effect as the third embodiment can be achieved by the fourth embodiment.

In addition, according to the fourth embodiment, for example, by installing the first thermal camera and the second thermal camera at locations separated from each other, it is possible to determine whether or not the object is a living body, even when the object moves.

In addition, according to the fourth embodiment, when it is determined that the object is not a living body, the guard or the watchman who receives the notice can take appropriate measures promptly based on the notice because the notice means is provided to notify the fact.

Next, a modification of the fourth embodiment will be described.

In the above fourth embodiment, an example in which after the living body determination means 12$k$ determines that the object is a living body, the authentication control means 12$n$ causes the authentication apparatus 60 to perform a face authentication of the object (step S22) was described, but it is not limited to this.

For example, before the living body determination means 12$k$ determines that the object is a living body (for example, before step S20), the authentication control means 12$n$ may cause the authentication apparatus 60 to perform a face authentication of the object.

For example, the authentication control means 12$n$ may cause the authentication apparatus 60 to perform a face authentication of the object in parallel with the processing of steps S10A to S21.

Next, a living body detection system 1C is described in detail as a fifth embodiment of this disclosure.

Figure 24:
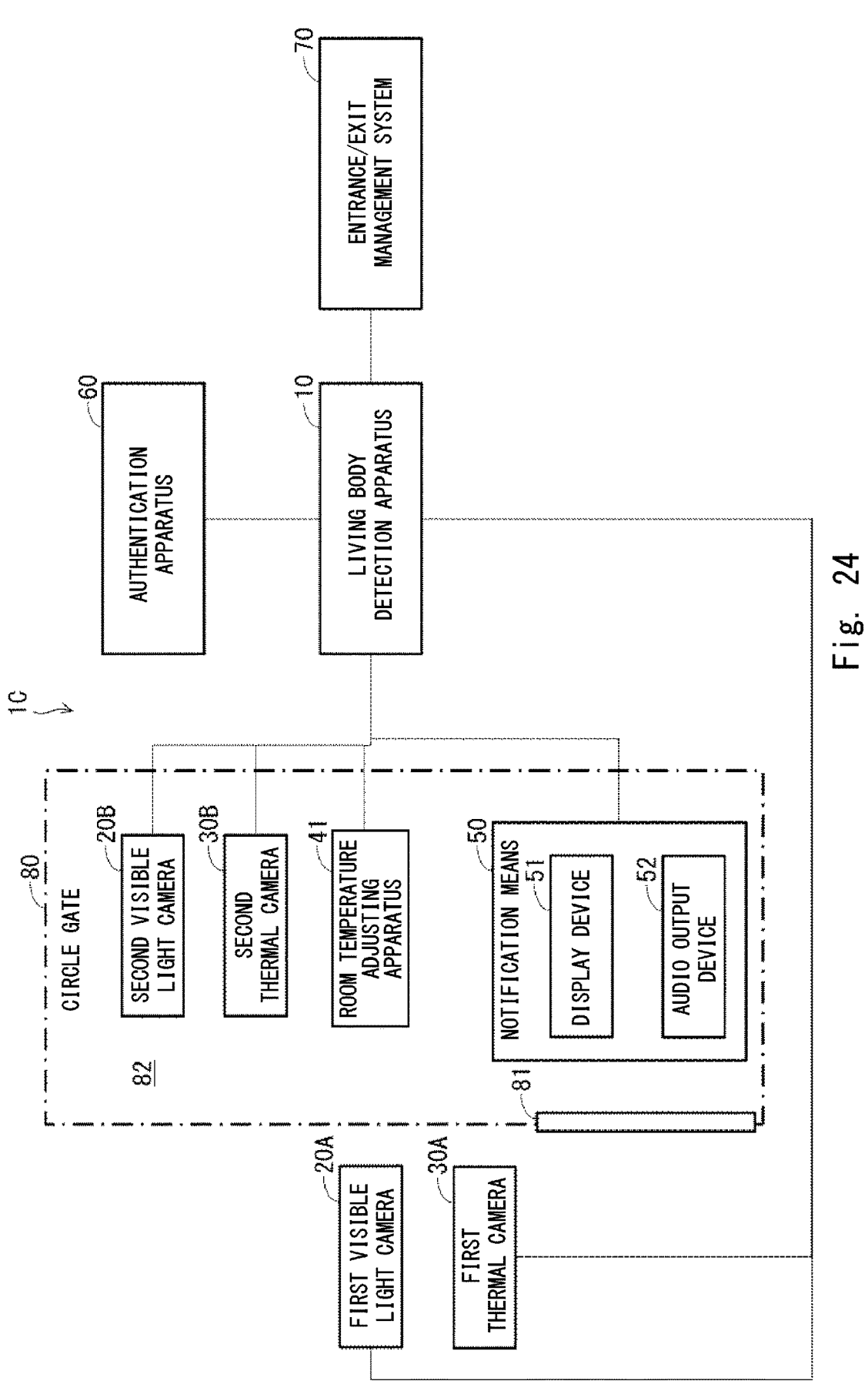
FIG. 24 is a block diagram showing the configuration of the living body detection system 1C according to the fifth embodiment.

FIG. 24 is a block diagram showing the configuration of the living body detection system 1C according to the fifth embodiment.

Hereafter, the differences from the third embodiment will be mainly explained, and the same components will be denoted by the same symbols, and the explanation will be omitted as appropriate.

As shown in FIG. 24, the living body detection system 1C according to the fifth embodiment comprise the first visible light camera 20A, the second visible light camera 20B, the first thermal camera 30A, the second thermal camera 30B and the circle gate 80 having the space 82 isolated from the outside.

Figure 25:
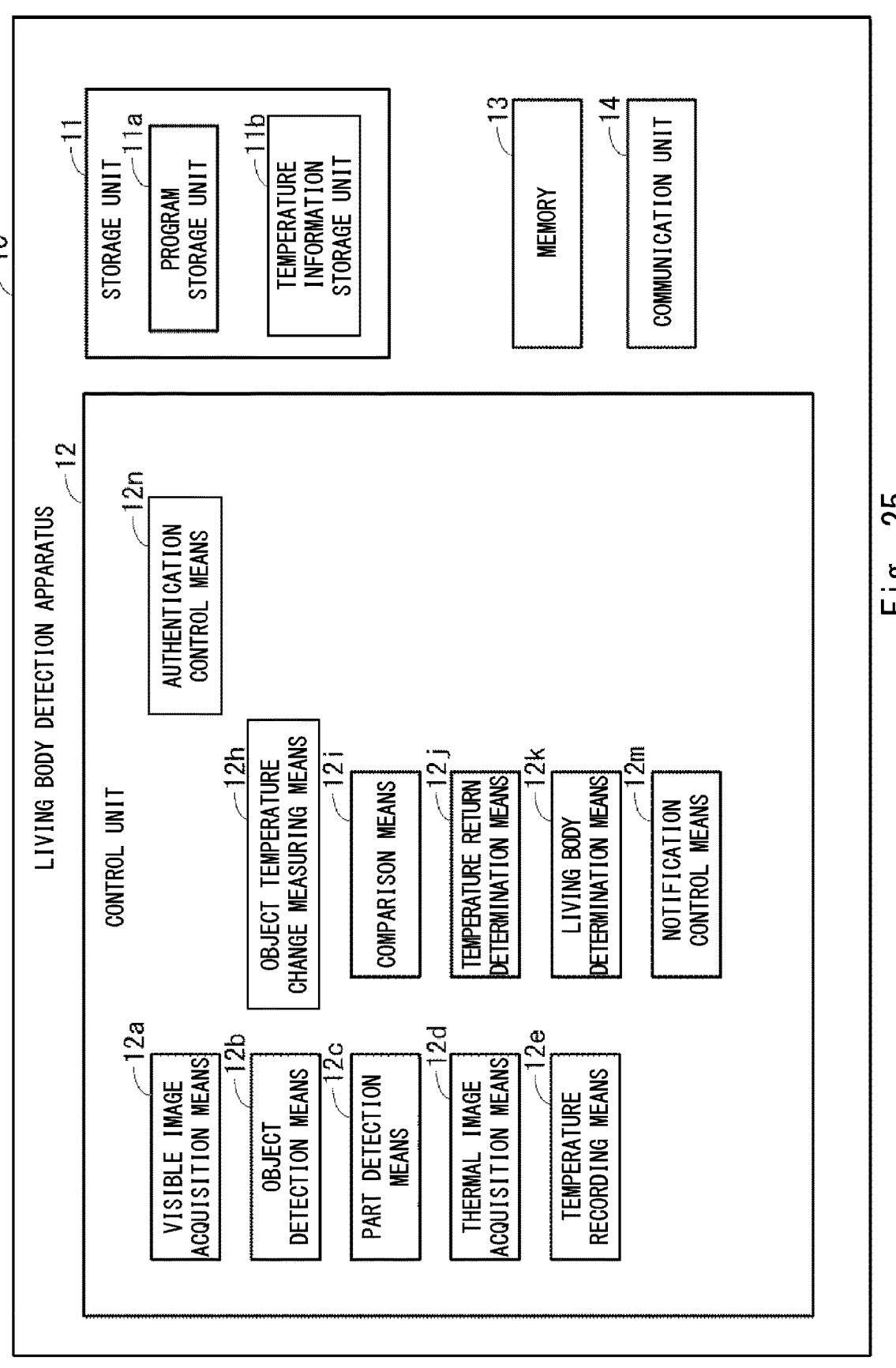
FIG. 25 is a block diagram showing the configuration of the living body detection apparatus 10 according to the fifth embodiment.

The first visible light camera 20A and the first thermal camera 30A are installed near the door 81 outside the space 82 of the circle gate 80, for example. The second visible light camera 20B and the second thermal camera 30B are installed in the space 82 of the circle gate 80. The room temperature adjusting apparatus 41 (an air conditioner, etc.) is installed in the space 82 of the circle gate 80. The room temperature adjusting apparatus 41 is an example of the surface temperature change means in this disclosure. As shown in FIG. 25, temperature control means 12$f$ and temperature setting means 12$g$ are omitted. FIG. 25 is a block diagram showing the configuration of the living body detection apparatus 10 according to the fifth embodiment.

Next, an example of the operation of the living body detection apparatus 10 according to the fifth embodiment will be described.

Figure 26:
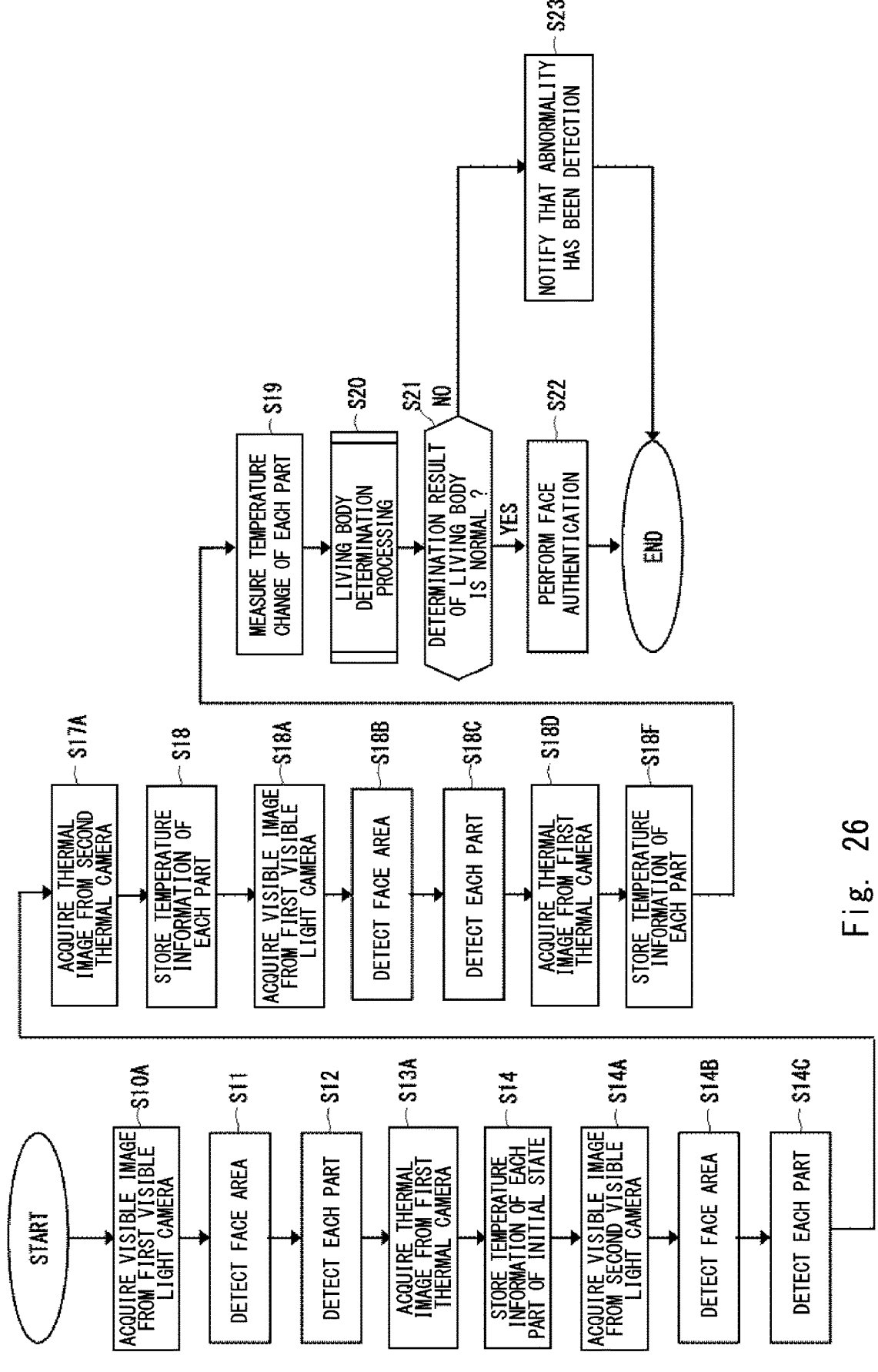
FIG. 26 is a flowchart of one example of the operation of the living body detection apparatus 10 according to the fifth embodiment.

FIG. 26 is a flowchart of one example of the operation of the living body detection apparatus 10 according to the fifth embodiment.

The following processing is realized by the control unit 12 (a processor) executing a program read from the program storage unit 11$a$ into a RAM (not shown). Hereafter, it is assumed that the space 82 of the circle gate 80 is setting lower (or higher) than the ambient temperature outside the space 82 of the circle gate 80 by the room temperature adjusting apparatus 41 (an air conditioner, etc.).

First, the visible image acquisition means 12$a$ acquires a visible image including an object (the object attempting to enter the space 82 in the circle gate 80) taken by the first visible light camera 20A from the first visible light camera 20A installed near the door 81 of the circle gate 80 (step S10A). Here, it is assumed that a visible image I including the face of the object Ob shown in FIG. 8 is acquired.

Next, the object detection means 12$b$ detects the face area A1 of the object Ob in the visible image I acquired by the visible image acquisition means 12$a$ (step S11).

Next, the part detection means 12$c$ detects each part (a first part that is relatively likely to change temperature, a second part that is relatively unlikely to change temperature) in the face area A1 detected by the object detection means 12$b$ (step S12). Here, as shown in FIG. 8, it is assumed that the ears e1 is detected as the first part that is relatively likely to change temperature, and the forehead e2 as the second part that is relatively unlikely to change temperature change.

Figure 27:
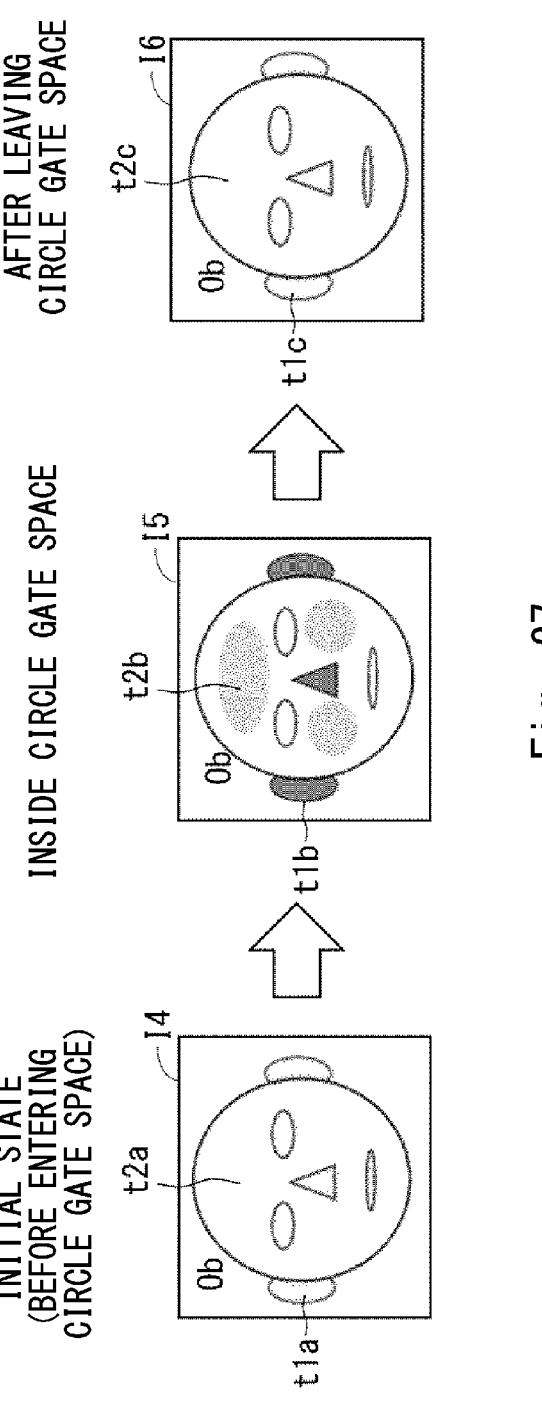
FIG. 27 shows an example of thermal images 14-16.

Next, the thermal image acquisition means 12$d$ acquires from the first thermal camera 30A a thermal image (see, e.g., symbol 14 in FIG. 27) including the object taken by the first thermal camera 30A (the same object as the one taken by the first visible light camera 20A) installed near the door 81 of the circle gate 80 (step S13A).

Next, the temperature recording means 12$e$ stores temperature information of the surface temperature of each part (in the thermal image 14 acquired by the thermal image acquisition means 12$d$) detected by the part detection means 12$c$ in the temperature information storage unit 11$b$ (step S14).

Here, it is assumed that t1$a$ (see FIG. 27) as the surface temperature of the ears in the initial state (before entering the space 82 of the circle gate 80) and t2$a$ (see FIG. 27) as the surface temperature of the forehead in the initial state (before entering the space 82 of the circle gate 80) are stored in the temperature information storage unit 11$b$, respectively.

Next, the visible image acquisition means 12a acquires a visible image including the object taken by the second visible light camera 20B from the second visible light camera 20B installed in the space 82 of the circle gate 80 as in step S10A (step S14A).

Next, the object detection means 12b detects the face area of the object Ob in the visible image acquired by the visible image acquisition means 12a as in step S11 (step S14B).

Next, the part detection means 12c detects each part (the first part that is relatively likely to change temperature, the second part that is relatively unlikely to change temperature) in the face area detected by the object detection means 12b as in step S12 (step S14C).

Next, the thermal image acquisition means 12d acquires from the second thermal camera 30B a thermal image (see, e.g., symbol 15 in FIG. 27) including the object taken by the second thermal camera 30B installed in the space 82 of the circle gate 80 (step S17A).

Next, the temperature recording means 12e stores temperature information of the surface temperature of each part (in the thermal image I5 acquired by the thermal image acquisition means 12d) detected by the part detection means 12c in the temperature information storage unit 11b (step S18).

Here, it is assumed that t1b (see FIG. 5) as the surface temperature of the ears in the space 82 of the circle gate 80 and t2b (see FIG. 5) as the surface temperature of the forehead in the space 82 of the circle gate 80 are stored in the temperature information storage unit 11b, respectively.

Next, the visible image acquisition means 12a acquires a visible image including the object (the object exiting the space 82 in the circle gate 80) taken by the first visible light camera 20A from the first visible light camera 20A installed near the door 81 of the circle gate 80 (step S18A). Here, it is assumed that a visible image I including the face of the object Ob shown in FIG. 8 is acquired.

Next, the object detection means 12b detects the face area A1 of the object Ob in the visible image I acquired by the visible image acquisition means 12a (step S18B).

Next, the part detection means 12c detects each part (the first part that is relatively likely to change temperature, the second part that is relatively unlikely to change temperature) in the face area A1 detected by the object detection means 12b (step S18C). Here, as shown in FIG. 8, it is assumed that the ears e1 is detected as the first part that is relatively likely to change temperature, and the forehead e2 as the second part that is relatively unlikely to change temperature change.

Next, the thermal image acquisition means 12d acquires from the first thermal camera 30A a thermal image (see, e.g., symbol 16 in FIG. 27) including the object taken by the first thermal camera 30A (the same object as the one taken by the first visible light camera 20A) installed near the door 81 of the circle gate 80 (step S18D).

Next, the temperature recording means 12e stores temperature information of the surface temperature of each part (in the thermal image 16 acquired by the thermal image acquisition means 12d) detected by the part detection means 12c in the temperature information storage unit 11b (step S18F).

Here, it is assumed that tic (see FIG. 27) as the surface temperature of the ears after exiting the space 82 of the circle gate 80 and t2c (see FIG. 27) as the surface temperature of the forehead after exiting the space 82 of the circle gate 80 are stored in the temperature information storage unit 11b, respectively.

Next, the object temperature change measuring means 12h measures the temperature change of the object (for example, the first part and the second part detected by the part detection means 12c) detected by the object detection means 12b, based on the temperature information of the surface temperature for each part stored in the temperature information storage unit 11b (step S19).

Here, since the surface temperatures t1a, t1b and t1c of the ears and the surface temperatures t2a, t2b and t2c of the forehead are stored in the temperature information storage unit 11b as the temperature information of the surface temperature of each part, the object temperature change measuring means 12h measures (calculates) the temperature changes t1a-t1b and t1b-t1c of the surface temperature of the ears (the first part) and the temperature changes t2a-t2b and t2b-t2c of the surface temperature of the forehead (the second part) as the temperature changes of the surface temperature of the object.

Next, the living body determination means 12k performs the living body determination processing to determine whether or not the object is a living body (step S20). Since the specific example of this living body determination processing has already been described, its explanation is omitted.

When the determination result of the living body determination processing (step S20) is living body detection results normal (step S21: YES), a face authentication of the object is performed (step S22). For example, the authentication control means 12n causes the authentication apparatus 60 for performing authentication to perform the face authentication of the object by sending a face authentication request containing a face image (visible image) of an object to the authentication apparatus 60 for performing face authentication. The authentication result (the collation result) is notified to the entrance/exit management system 70.

On the other hand, when the determination result of the living body determination processing (step S20) is living body detection results abnormal (step S21: NO), notification means 12p notifies that an abnormality has been detection (step S23). For example, so as to display the fact that the abnormality has been detection on the monitor or the like, which is visually observed by the guard or the watchman, the notification means 12p notifies the fact that the abnormality has been detection on the predetermined apparatus via the communication unit 14. Or, when the determination result of the living body determination processing (step S20) is living body detection results abnormal (step S21: NO), the processing may be terminated without notification that the above has been detection.

The same effect as the third embodiment can be achieved by the fifth embodiment. Next, a modification of the fifth embodiment will be described.

In the fifth embodiment above, the example in which the second thermal camera 30B is installed in the space 82 of the circle gate 80 was described, but it is not limited to this. For example, the second thermal camera 30B may be installed outside the space 82 of the circle gate 80. Even if the second thermal camera 30B is installed outside the space 82 of the circle gate 80, the temperature of the object in the space 82 can be measured from outside the space 82 by forming the circle gate 80 with a transparent wall, for example.

Moreover, by installing the second thermal camera 30B outside the space 82 of the circle gate 80 and adjusting the angle of the second thermal camera 30B, by the second thermal camera 30B, the functions of the first thermal camera 30A and the second thermal camera 30B can be realized by one thermal camera.

By using one thermal camera in this way, it becomes easier to acquire the temperature change of the object's face.

In the above fifth embodiment, the example in which the first thermal camera 30A installed near the door 81 outside the space 82 of the circle gate 80 takes an object attempting to enter the space 82 of the circle gate 80, the second thermal camera installed in the space 82 of the circle gate 80 takes the object in the space 82 of the circle gate 80, and the first thermal camera 30A installed near the door 81 outside the space 82 of the circle gate 80 images an object attempting to enter the space 82 of the circle gate 80 was described, but it is not limited to this.

Figure 28:
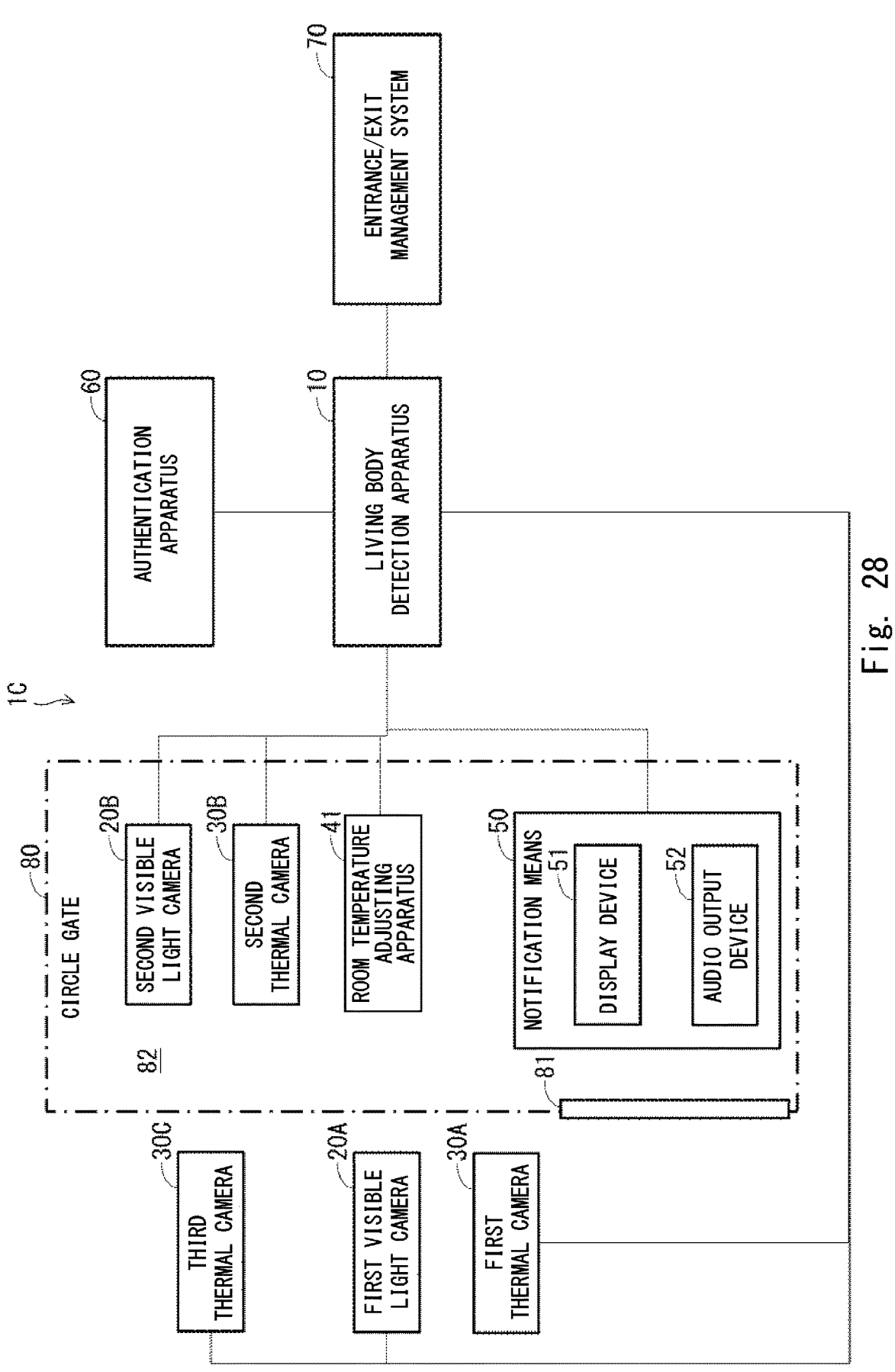
FIG. 28 is a block diagram showing the configuration of the living body detection system 1C (a modified example) according to the fifth embodiment.

For example, as shown in FIG. 28, for example, a third thermal camera 30C may be installed outside the space 82 of the circle gate 80 to take the object exited from the space 82 of the circle gate 80 and record temperature information (a processing corresponding to steps S18D and S18F in FIG. 26), and a living body detection may be performed considering the temperature change of the object exited from the space 82 of the circle gate 80. FIG. 28 is a block diagram showing the configuration of the living body detection system 1C (a modified example) according to the fifth embodiment.

Next, variations of the second embodiment to the fifth embodiment will be described.

In the second embodiment to the fourth embodiment, an example of determining whether or not an object is a living body based on the temperature change of the surface temperature of the face (the part) of the object was described, but this is not limited to the above. For example, it may be determined whether or not the object is a living body based on temperature changes in the surface temperatures of the hands, neck, and legs (the part) other than the object's face.

In the second embodiment to the fourth embodiment, an example using a thermal camera 30 to measure the surface temperature of an object (a part) was described, but it is not limited to this. If the surface temperature of the object (the part) can be measured, other non-contact temperature measuring means may be used, or contact temperature measuring means may be used.

In the above-described first and second embodiments, the program may be stored in various types of non-transitory computer readable media and thereby supplied to computers. The non-transitory computer readable media includes various types of tangible storage media. Examples of the non-transitory computer readable media include a magnetic recording medium (such as a flexible disk, a magnetic tape, and a hard disk drive), a magneto-optic recording medium (such as a magneto-optic disk), a CD-ROM (Read Only Memory), CD-R, CD-R/W, and a semiconductor memory (such as a mask ROM, a PROM (Programmable ROM), an EPROM (Erasable PROM), a flash ROM, and a RAM (Random Access Memory)). Further, the programs may be supplied to computers by using various types of transitory computer readable media. Examples of the transitory computer readable media include an electrical signal, an optical signal, and an electromagnetic wave. The transitory computer readable media can be used to supply programs to a computer through a wired communication line (e.g., electric wires and optical fibers) or a wireless communication line.

All the numeral values mentioned in the above-described example embodiments are merely examples, and needless to say, numeral values different from them can be uses as desired.

The above-described example embodiments are merely examples in all the aspects thereof. The present invention should not be limited by the descriptions of the above-described example embodiments. The present invention may be carried out in various other forms without departing from the spirit or main features of the invention.

Further, the whole or part of the example embodiments disclosed above can be described as, but not limited to, the following supplementary notes.

(Supplementary Note 1)

An information processing apparatus comprising:

object temperature change measuring means for measuring a temperature change of a surface temperature of an object, and living body determination means for determining whether or not the object is a living body based on the temperature change.

(Supplementary Note 2)

The information processing apparatus according to Supplementary note 1, further comprising:

visible image acquisition means for acquiring a visible image including the object taken by a visible light camera;

thermal image acquisition means for acquiring a thermal image including the object taken by a thermal camera; and object detection means for detecting the object in the visible image; wherein the object temperature change measuring means measures the temperature change of the object detected based on the thermal image.

(Supplementary Note 3)

The information processing apparatus according to Supplementary note 2, further comprising:

part detection means for detecting at least one part in the object detected by the object detection means; wherein the object temperature change measuring means measures the temperature change of the part based on the thermal image, the living body determination means determines whether or not the object is a living body based on the temperature change of the part.

(Supplementary Note 4)

The information processing apparatus according to Supplementary note 3, wherein the part includes a first part that is relatively likely to change temperature and a second part that is relatively unlikely to change temperature, the object temperature change measuring means measures the temperature change of the first part and the temperature change of the second part based on the thermal image, the information processing apparatus further comprises:

comparison means for comparing a temperature change of the first part with a temperature change of the second part; wherein the living body determination means determines whether or not the object is a living body based on the comparison result of the comparison means.

(Supplementary Note 5)

The information processing apparatus according to any one of Supplementary notes 1 to 3, further comprising:

temperature return determination means for determining whether or not the object surface temperature has returned to the original surface temperature before the change; wherein the living body determination means determines whether or not the object is a living body based on the determination result of the temperature return determination means.

(Supplementary Note 6)

The information processing apparatus according to any one of Supplementary notes 1 to 3, further comprising:

comparison means for comparing a change pattern of a surface temperature of the object with a change pattern of a surface temperature of a reference person; wherein the living body determination means determines whether or not the object is a living body based on the comparison result of the comparison means.

(Supplementary Note 7)

The information processing apparatus according to any one of Supplementary notes 1 to 6, further comprising:

temperature control means for controlling a surface temperature change means that changes a surface temperature of the object.

(Supplementary Note 8)

The information processing apparatus according to Supplementary note 7, wherein the surface temperature change means is a wind blowing means for blowing wind of a predetermined temperature to the object.

(Supplementary Note 9)

The information processing apparatus according to Supplementary note 8, further comprising:

temperature setting means for setting a predetermined temperature.

(Supplementary Note 10)

The information processing apparatus according to Supplementary note 8 or 9, further comprising:

notification control means for causing notification means to notify that a wind will blow from now on before the wind blowing means blows the wind to the object.

(Supplementary Note 11)

The information processing apparatus according to Supplementary note 7, wherein the surface temperature change means is a room temperature adjusting apparatus installed in a space isolated from outside.

(Supplementary Note 12)

The information processing apparatus according to any one of Supplementary notes 1 to 11, wherein the living body determination means determines whether or not the object is a living body, considering a result of comparison between a change pattern of a surface temperature of the object and a change pattern of a surface temperature of a reference non-person.

(Supplementary Note 13)

The information processing apparatus according to any one of Supplementary notes 8 to 10, wherein the living body determination means determines whether or not the object is a living body, considering a reaction of the object when the wind blowing means blows the wind to the object.

(Supplementary Note 14)

The information processing apparatus according to any one of Supplementary notes 1 to 11, wherein the living body determination means determines whether or not the object is a living body, considering a surface condition of the object before and after changing a surface temperature.

(Supplementary Note 15)

The information processing apparatus according to any one of Supplementary notes 1 to 11, wherein the living body determination means determines whether or not the object is a living body, considering a temperature change in a background of the object.

(Supplementary Note 16)

The information processing apparatus according to any one of Supplementary notes 1 to 6, further comprising:

notification control means for causing notification means to notify a content that encourages actions to change the object's body temperature before the object temperature change measuring means measures a temperature change of a surface temperature of the object.

(Supplementary Note 17)

The information processing apparatus according to Supplementary note 2, wherein the thermal camera includes a first thermal camera and a second thermal camera.

(Supplementary Note 18)

The information processing apparatus according to any one of Supplementary notes 1 to 17, further comprising:

authentication control means for causing the authentication apparatus performing the face authentication to perform the face authentication of the object; wherein the authentication control means causes the authentication apparatus to perform the face authentication of the object after the living body determination means determines that the object is a living body, the information processing apparatus further comprises:

notification means for notifying to that effect when the living body determination means determines that the object is not a living body.

(Supplementary Note 19)

A living body detection system comprising:

object temperature change measuring means for measuring a temperature change of a surface temperature of an object, and living body determination means for determining whether or not the object is a living body based on the temperature change.

(Supplementary Note 20)

A living body detection system according to Supplementary note 19, further comprising:

a visible light camera;

a thermal camera;

visible image acquisition means for acquiring a visible image including the object taken by the visible light camera;

thermal image acquisition means for acquiring a thermal image including the object taken by the thermal camera;

object detection means for detecting the object in the visible image; wherein the object temperature change measuring means measures the temperature change of the object detected based on the thermal image.

(Supplementary Note 21)

A living body detection method comprising:

object temperature change measuring step measuring a temperature change of a surface temperature of an object, and living body determination step determining whether or not the object is a living body based on the temperature change.

(Supplementary Note 22)

The living body detection method according to Supplementary note 21, further comprising:

visible image acquisition step acquiring a visible image including the object taken by a visible light camera;

thermal image acquisition step acquiring a thermal image including the object taken by a thermal camera; and object detection step detecting the object in the visible image; wherein

27 the object temperature change measurement step measures the temperature change of the object detected based on the thermal image.

(Supplementary Note 23)

A non-transitory computer readable medium storing a program for causing an electronic device to execute the following steps of:

object temperature change measuring step measuring a temperature change of a surface temperature of an object, and living body determination step determining whether or not the object is a living body based on the temperature change.

(Supplementary Note 24)

The non-transitory computer readable medium according to Supplementary note 23, further storing a program for causing the electronic device to execute the following steps of:

visible image acquisition step acquiring a visible image including the object taken by a visible light camera;

thermal image acquisition step acquiring a thermal image including the object taken by a thermal camera; and object detection step detecting the object in the visible image; wherein the object temperature change measurement step measures the temperature change of the object detected based on the thermal image.

REFERENCE SIGNS LIST 1, 1A, 1B LIVING BODY DETECTION SYSTEM
10 LIVING BODY DETECTION APPARATUS
11 STORAGE UNIT
11a PROGRAM STORAGE UNIT
11b TEMPERATURE INFORMATION STORAGE UNIT
12 CONTROL UNIT
12a VISIBLE IMAGE ACQUISITION MEANS
12b OBJECT DETECTION MEANS
12c PART DETECTION MEANS
12d THERMAL IMAGE ACQUISITION MEANS
12e TEMPERATURE RECORDING MEANS
12f TEMPERATURE CONTROL MEANS
12g TEMPERATURE SETTING MEANS
12h OBJECT TEMPERATURE CHANGE MEASURING MEANS
12i COMPARISON MEANS
12j TEMPERATURE RETURN DETERMINATION MEANS
12k LIVING BODY DETERMINATION MEANS
12m NOTIFICATION CONTROL MEANS
12n AUTHENTICATION CONTROL MEANS
12p NOTIFICATION MEANS
13 MEMORY
14 COMMUNICATION UNIT
20 VISIBLE LIGHT CAMERA
20A FIRST VISIBLE LIGHT CAMERA
20B SECOND VISIBLE LIGHT CAMERA
30 THERMAL CAMERA
30A FIRST THERMAL CAMERA
30B SECOND THERMAL CAMERA
40 WIND BLOWING MEANS
41 ROOM TEMPERATURE ADJUSTING APPARATUS
50 NOTIFICATION MEANS
51 DISPLAY DEVICE
52 AUDIO OUTPUT DEVICE
60 AUTHENTICATION APPARATUS

28

70 ENTRANCE/EXIT MANAGEMENT SYSTEM
80 CIRCLE GATE
81 DOOR
82 SPACE
A1 FACE AREA
I VISIBLE IMAGE
I1-I3 THERMAL IMAGE
Ob OBJECT
e1 EAR
e2 FOREHEAD
t1a, t1b SURFACE TEMPERATURE

What is claimed is:

1. An information processing apparatus comprising:
at least one memory storing instructions; and
at least one processor configured to execute the instructions to:
acquire a visible light image that includes an object and is taken by a visible light camera,
acquire a thermal image that includes the object and is taken by a thermal camera,
detect the object in the visible light image,
measure a temperature change of a surface temperature of the object, and
determine whether or not the object is a living body based on the temperature change, wherein
the temperature change of the object is measured based on the thermal image, and
the at least one processor is further configured to execute the instructions to:
detect at least one part in the object detected, wherein the at least one part includes a first part that is relatively likely to change temperature and a second part that is relatively unlikely to change temperature,
measure a temperature change of the first part and a temperature change of the second part based on the thermal image,
compare the temperature change of the first part with the temperature change of the second part, and
determine whether or not the object is a living body based on the comparison result.

2. The information processing apparatus according to claim 1, wherein
the at least one processor is further configured to execute the instructions to:
determine whether or not the surface temperature of the object has returned to an original surface temperature before the temperature change, and
determine whether or not the object is a living body based on the determination result.

3. The information processing apparatus according to claim 1, wherein
the at least one processor is further configured to execute the instructions to:
compare a change pattern of the surface temperature of the object with a change pattern of a surface temperature of a reference person, and
determine whether or not the object is a living body based on the comparison result.

4. The information processing apparatus according to claim 1, wherein
the at least one processor is further configured to execute the instructions to control an apparatus that changes the surface temperature of the object.

5. The information processing apparatus according to claim 4, wherein
the apparatus is a blower for blowing wind of a predetermined temperature to the object.

6. The information processing apparatus according to claim 5, wherein
the at least one processor is further configured to execute the instructions to cause a notification device to notify that a wind will blow from now on before the blower blows the wind to the object.

7. The information processing apparatus according to claim 4, wherein
the apparatus is a room temperature adjusting apparatus installed in a space isolated from outside.

8. The information processing apparatus according to claim 1, wherein
the at least one processor is further configured to execute the instructions to determine whether or not the object is a living body, considering a result of a comparison between a change pattern of the surface temperature of the object and a change pattern of a surface temperature of a reference non-person.

9. The information processing apparatus according to claim 1, wherein
the at least one processor is further configured to execute the instructions to determine whether or not the object is a living body, considering a reaction of the object when a blower blows wind to the object.

10. The information processing apparatus according to claim 1, wherein
the at least one processor is further configured to execute the instructions to determine whether or not the object is a living body, considering a surface condition of the object before and after changing the surface temperature.

11. The information processing apparatus according to claim 1, wherein
the at least one processor is further configured to execute the instructions to determine whether or not the object is a living body, considering a temperature change in a background of the object.

12. The information processing apparatus according to claim 1, wherein
the at least one processor is further configured to execute the instructions to cause a notification device to notify a content that encourages actions to change a body temperature of the object before measuring the temperature change of the surface temperature of the object.

13. The information processing apparatus according to claim 1, wherein
the at least one processor is further configured to execute the instructions to:
cause an authentication apparatus performing a face authentication to perform face authentication of the object,
cause the authentication apparatus to perform the face authentication of the object after determining that the object is a living body, and
notify to that effect when it is determined that the object is not a living body.

14. A living body detection method stored on a memory and executable by a processor, the method comprising:
acquiring a visible light image that includes an object and is taken by a visible light camera,
acquiring a thermal image that includes the object and is taken by a thermal camera,
detecting the object in the visible light image,
measuring a temperature change of a surface temperature of the object, and
determining whether or not the object is a living body based on the temperature change, wherein
the temperature change of the object is measured based on the thermal image, and
the method further comprises:
detecting at least one part in the object detected, wherein the at least one part includes a first part that is relatively likely to change temperature and a second part that is relatively unlikely to change temperature;
measuring a temperature change of the first part and a temperature change of the second part based on the thermal image;
comparing the temperature change of the first part with the temperature change of the second part; and
determining whether or not the object is a living body based on the comparison result.

15. A non-transitory computer readable medium storing a program for causing an electronic device to execute operations comprising:
acquiring a visible light image that includes an object and is taken by a visible light camera,
acquiring a thermal image that includes the object and is taken by a thermal camera,
detecting the object in the visible light image,
measuring a temperature change of a surface temperature of the object, and
determining whether or not the object is a living body based on the temperature change, wherein
the temperature change of the object is measured based on the thermal image, and
the program causes the electronic device to execute operations further comprising:
detecting at least one part in the object detected, wherein the at least one part includes a first part that is relatively likely to change temperature and a second part that is relatively unlikely to change temperature;
measuring a temperature change of the first part and a temperature change of the second part based on the thermal image;
comparing the temperature change of the first part with the temperature change of the second part; and
determining whether or not the object is a living body based on the comparison result.

\* \* \* \* \*